(12) United States Patent
Albertella

(10) Patent No.: US 12,303,521 B2
(45) Date of Patent: May 20, 2025

(54) METHODS FOR TREATING LIVER CANCERS USING AN ORALLY ADMINISTERED DIOXOLANE NUCLEOTIDE IN COMBINATION WITH AN ANTI-PD1 OR ANTI-PDL1 MONOCLONAL ANTIBODY

(71) Applicant: MEDIVIR AB, Huddinge (SE)

(72) Inventor: Mark Albertella, Huddinge (SE)

(73) Assignee: MEDIVIR AB, Stockholm (SE)

( * ) Notice: Subject to any disclaimer, the term of this patent is extended or adjusted under 35 U.S.C. 154(b) by 725 days.

(21) Appl. No.: 17/431,686

(22) PCT Filed: Feb. 17, 2020

(86) PCT No.: PCT/SE2020/050175
§ 371 (c)(1),
(2) Date: Aug. 17, 2021

(87) PCT Pub. No.: WO2020/171757
PCT Pub. Date: Aug. 27, 2020

(65) Prior Publication Data
US 2022/0117983 A1    Apr. 21, 2022

(30) Foreign Application Priority Data

Feb. 18, 2019    (SE) .................................. 1950202-0

(51) Int. Cl.
| | | |
|---|---|---|
| *A61K 31/675* | (2006.01) | |
| *A61K 45/06* | (2006.01) | |
| *A61P 35/00* | (2006.01) | |
| *C07K 16/28* | (2006.01) | |
| *A61K 39/00* | (2006.01) | |

(52) U.S. Cl.
CPC ............ *A61K 31/675* (2013.01); *A61K 45/06* (2013.01); *A61P 35/00* (2018.01); *C07K 16/2827* (2013.01); *A61K 2039/505* (2013.01)

(58) Field of Classification Search
CPC ................... A61K 31/675; A61K 45/06; A61K 2039/505; A61K 39/39558; A61K 2300/00; A61P 35/00; C07K 16/2827; C07K 2317/24; C07K 2317/76
See application file for complete search history.

(56) References Cited

U.S. PATENT DOCUMENTS

2024/0024342 A1* 1/2024 Oberg ...................... A61P 35/04

FOREIGN PATENT DOCUMENTS

| | | | |
|---|---|---|---|
| CN | 109069509 | A | 12/2018 |
| JP | 2018534321 | A | 11/2018 |
| WO | 2013079174 | A1 | 6/2013 |
| WO | 2016030335 | A1 | 3/2016 |
| WO | 2016172273 | A1 | 10/2016 |
| WO | 2017151044 | A1 | 9/2017 |
| WO | 2018053106 | A1 | 3/2018 |

OTHER PUBLICATIONS

Bethell, R. et al, "Selective Targeting of the Liver with the Nucleotide Prodrug MIV-818 for the treatment of Liver Cancers." Hepatol Int., 2017, vol. 11, (Suppl 1): S67.
Constantinidou, A. et al, "Targeting Programmed Cell Death—1 (PD-1) and Ligand (PD-L1): A New Era in Cancer Active Immunotherapy", Pharmacology & Therapeutics, 2018, vol. 194, pp. 84-166.
Oberg, F.G. et al, "MIV-818 stimulates an antitumor immune response in vitro and enhances the effects of pembrolizumab", 2019, International Conference of Molecular Targets and Cancer Therapeutics Poster.
Wu et al., "Acute liver failure caused by pembrolizumab in a patient with pulmonary metastatic liver cancer", Medicine, 2017, vol. 96:51, pp. 1-4.
Extended European Search Report for corresponding European application No. 20759362, issued on Oct. 3, 2022.
Japanese Office Action issued in corresponding patent application, Patent application JP2021-548235A. Office action issued on Feb. 16, 2024 attached with machine translation.
International Search Report issued for PCT/SE2020/050175 on Mar. 10, 2020.
English Translation of Chinese Second Office Action in corresponding national stage application issued on Aug. 30, 2024.
English Translation of the Chinese Decision of Rejection from corresponding national phase application issued on Nov. 27, 2024.
Kequn, Chai, "Basics and Clinical Practice of Integrated Traditional Chinese and Western Medicine in Diagnosis and Treatment of Digestive System Tumors", Shanghai Science and Technology Press, Diagnosis and Treatment of Primary Liver Cancer with Integrated Traditional Chinese and Western Medicine, 2017, pp. 163-164.

(Continued)

*Primary Examiner* — Sun Jae Yoo
(74) *Attorney, Agent, or Firm* — Susan W. Gorman; Gorman IP Law, APC

(57) ABSTRACT

Use of a compound of the formula I:

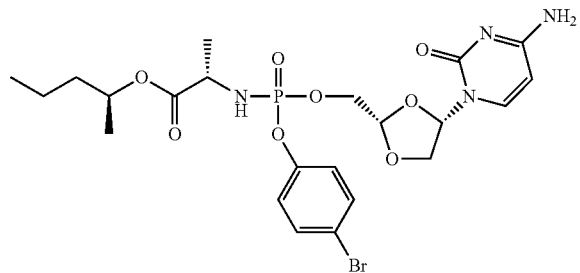

or a pharmaceutically acceptable salt thereof, in the therapy of a liver cancer in a mammal, characterized by the concurrent or sequential treatment of the mammal with a monoclonal antibody which blocks the binding of PD-L1 and/or PD-L2 to PD-1.

18 Claims, 19 Drawing Sheets

(56) References Cited

OTHER PUBLICATIONS

Su, Chunxia, "New Progress in Immunotherapy of Lung Cancer," Shanghai Science Popularization Press, PD1/PD-L1 Immunotherapy Mechanism, 2018, pp. 60-63.

* cited by examiner

METHODS FOR TREATING LIVER CANCERS USING AN ORALLY ADMINISTERED DIOXOLANE NUCLEOTIDE IN COMBINATION WITH AN ANTI-PD1 OR ANTI-PDL1 MONOCLONAL ANTIBODY

This Nonprovisional application is the National Phase Under 35 USC § 371 of PCT International Application No. PCT/SE2020/050175 filed on Feb. 17, 2020, which claims priority under 35 U.S.C. § 119 on Patent Application No. 1950202-0 filed in Sweden on Feb. 18, 2019, the entire contents of each of which are hereby incorporated by reference.

I. FIELD

Provided herein are methods for treating primary or metastatic cancers in the liver using an orally administered dioxolane nucleotide, MIV-818, its diastereomers or pharmaceutically acceptable salts thereof, in combination with a parenterally administered anti-PD1 or anti-PDL1 monoclonal antibody. Also provided herein are oral compositions of MIV-818, or pharmaceutically acceptable salts thereof, formulated for concurrent or sequential administration with an anti-PD1 or anti-PDL1 monoclonal antibody to a mammal afflicted with a liver tumour.

II. BACKGROUND

Primary liver cancer is the fifth most frequently diagnosed cancer globally and the second leading cause of cancer death. Liver cancers are malignant tumours that grow on the surface or inside the liver. They are formed from either the liver itself or from structures within the liver, including blood vessels or the bile duct.

The leading cause of liver cancer is viral infection with hepatitis B virus or hepatitis C virus. The cancer usually forms secondary to cirrhosis caused by these viruses. For this reason, the highest rates of liver cancer occur where these viruses are endemic, including East-Asia and sub-Saharan Africa. Other cancers located in the liver include liver metastases, also known as secondary liver cancer, which is a cancer that originate from organs elsewhere in the body and migrate to the liver. The liver is a common site for metastatic disease because of its rich, dual blood supply (the hepatic arery and portal vein. Metastatic tumours in the liver are twenty times more common that primary tumours. In 50% of all cases, the primary tumour is of the gastrointestinal tract. Other common sites include the breast, ovaries, bronchus and kidney.

The most frequent liver cancer, accounting for approximately 75% of all primary liver cancers, is hepatocellular carcinoma (HCC). HCC is a cancer formed by liver cells, known as hepatocytes that become malignant. Another type of cancer formed by liver cells is hepatoblastoma, which is specifically formed by immature liver cells. It is a rare malignant tumour that primarily develops in children, and accounts for approximately 1% of all cancers in children and 79% of all primary liver cancers under the age of 15.

Liver cancer can also form from other structures within the liver such as the bile duct, blood vessels and immune cells. Cancer of the bile duct (cholangiocarcinoma and cholangiocellular cystadenocarcinoma) accounts for approximately 6% of primary liver cancers. There is also a variant type of HCC that consists of both HCC and cholangiocarcinoma. Tumours of the liver blood vessels include angiosarcoma and hemangioendothelioma. Embryonal sarcoma and fibrosarcoma are produced from a type of connective tissue known as mesenchyme. Cancers produced from muscle in the liver are leiomyosarcoma and rhabdomyosarcoma. Other less common liver cancers include carcinosarcomas, teratomas, yolk sac tumours, carcinoid tumours and lymphomas. Lymphomas usually have diffuse infiltration to liver, but it may also form a liver mass in rare occasions.

Surgical resection is often the treatment of choice for non-cirrhotic livers. Increased risk of complications such as liver failure can occur with resection of cirrhotic livers. 5-year survival rates after resection has massively improved over the last few decades and can now exceed 50%. Recurrence rates after resection due to the spread of the initial tumour or formation of new tumours exceeds 70%. Liver transplantation can also be used in cases of HCC where this form of treatment can be tolerated and the tumour fits specific criteria (e.g., the Milan criteria). Less than 30-40% of individuals with HCC are eligible for surgery and transplant because the cancer is often detected late stage. Also, HCC can progress during the waiting time for liver transplants, which can ultimately prevent a transplant.

Percutaneous ablation is the only non-surgical treatment that can offer cure. There are many forms of percutaneous ablation, which consist of either injecting chemicals into the liver (ethanol or acetic acid) or producing extremes of temperature using radio frequency ablation, microwaves, lasers or cryotherapy. Of these, radio frequency ablation has one of the best reputations in HCC, but the limitations include inability to treat tumours close to other organs and blood vessels due to heat generation and the heat sync effect, respectively.

Systemic chemotherapeutics are not routinely used in HCC, although local chemotherapy may be used in a procedure known as transarterial chemoembolization (TACE). In this procedure, cytotoxic drugs such as doxorubicin or cisplatin with lipiodol are administered and the arteries supplying the liver are blocked by gelatine sponge or other particles. Because most systemic drugs have no efficacy in the treatment of HCC, research into the molecular pathways involved in the production of liver cancer produced sorafenib, a targeted therapy drug that prevents cell proliferation and blood cell growth in some circumstances.

Radiotherapy is not often used in HCC because the liver is not tolerant to radiation. Even with modern technology providing well targeted radiation to specific areas of the liver, collateral damage to surrounding liver tissue is a problem, emphasizing the need for better, "liver sparing" regimens. Dual treatments of radiotherapy plus chemoembolization, local chemotherapy, systemic chemotherapy or targeted therapy drugs may show benefit over radiotherapy alone.

International patent application WO2016/030335 discloses orally administered, liver-targeting dioxolane nucleotides, including the compound:

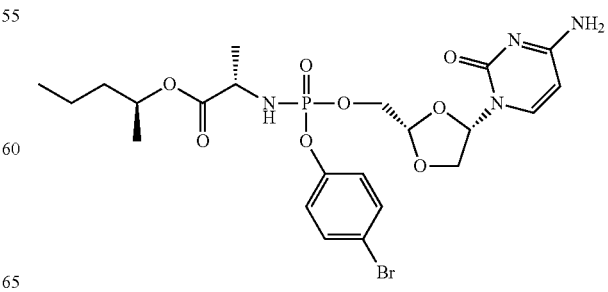

also known as MIV-818.

The importance of intact functions of immune surveillance in controlling outgrowth of neoplastic transformations has been widely known. High expression of PD-L1 (programmed death-ligand 1) on tumour cells has been found to correlate with poor prognosis and survival in various cancer types including ovarian carcinoma. Preclinical data suggests PD-1 (programmed death-1 or programmed cell death-1) pathway as a viable target in ovarian cancer. Clinical data on PD-1/PD-L1 inhibition in EOC are limited but in a Phase 1 study of the anti-PD-L1 antibody BMS-936559, one of seventeen patients with EOC had an objective response.

Inhibition of the immune checkpoint with antibodies directed at the PD-1 receptor on T cells or its ligand (PD-L1) on tumour cells has demonstrated promising antitumour activity in some, but not all, tumours, including melanoma and non-small cell lung cancer.

The PD-1 antagonist nivolumab, a fully human immunoglobulin G4 monoclonal antibody was approved in September 2017 by the FDA for the treatment of hepatic cancer, but only as second line treatment following failure of sorafenib.

Pembrolizumab, also known as MK-3475 and Keytruda, is a humanized monoclonal IgG4 antibody directed against human cell surface receptor PD-1 with potential immunopotentiating activity. Upon administration, pembrolizumab binds to PD-1, an inhibitory signaling receptor expressed on the surface of activated T cells, and blocks the binding to and activation of PD-1 by its ligands, which results in the activation of T-cell-mediated immune responses against tumour cells. The ligands for PD-1 include PD-L1, which is expressed on antigen presenting cells (APCs) and overexpressed on certain cancer cells, and PD-L2, which is primarily expressed on APCs. Activated PD-1 negatively regulates T-cell activation through the suppression of the PI3K/Akt pathway. However, there are reports of pembrolizumab-induced liver failure in pulmonary metastatic liver cancer (Wu et al, Medicine (Baltimore) 2017 96(51):e9431.

There still exists a significant unmet need for the treatment of primary and secondary liver, in particular, those that relapse after or are refractory to prior therapeutic treatments.

III. SUMMARY OF INVENTION

A first aspect of the invention provides the use of a compound of the formula:

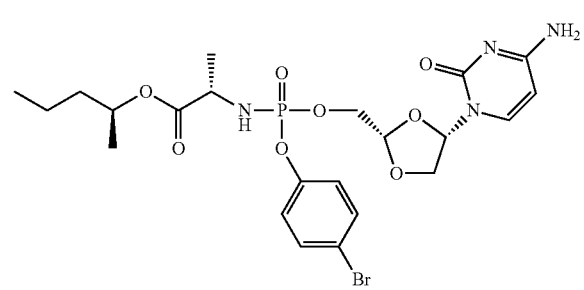 [SMILES: CCC[C@H](C)OC(=O)[C@H](C)NP(=O)(OC[C@H]1OC[C@@H](n2ccc(N)nc2=O)O1)Oc1ccc(Br)cc1]

its diastereomers or pharmaceutically acceptable salts thereof, in the therapy of a liver cancer in a mammal, characterized by the concurrent or sequential treatment of the mammal with a monoclonal antibody which blocks the binding of PD-L1 and/or PD-L2 to PD-1.

A second aspect of the invention provides a compound for use in a method for treating a mammal afflicted with a primary or secondary liver tumour, wherein the compound has the formula:

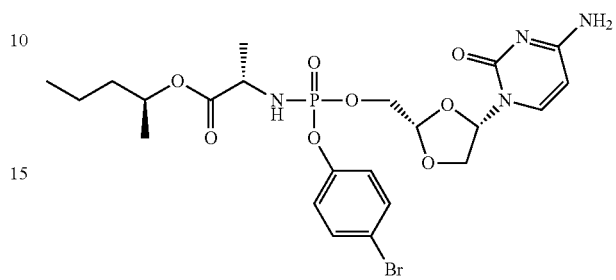

its diastereomers or pharmaceutically acceptable salts thereof, wherein the method comprises cyclically administering to the subject a therapeutically effective amount of the compound, its diastereomers or a pharmaceutically acceptable salt thereof, and a therapeutically effective amount of an anti-PD1 or anti-PDL1 monoclonal antibody, wherein the compound or a pharmaceutically acceptable salt thereof is administered orally.

The invention is based, at least in part, on the discovery that MIV-818 can stimulate the immune system in addition to having a direct anti-tumour effect on liver cancer cells. This activation of the immune system enhances the efficacy and/or tolerability of anti-PD1 or anti-PDL1 monoclonal antibodies to give an unexpected enhancement of anti-tumour activity, within the area of liver cancer (e.g., HCC). We hypothesise that this beneficial interaction may even extend to the treatment of liver metastases.

Without wishing to be bound by theory, we further hypothesise that the unexpected immune-stimulation of the combination of MIV-818 and agents such as PD1 and PDL1 antagonists, might lead to enhanced anti-tumour activity against extra-hepatic tumour lesions in addition to the primary lesions in the liver due to the abscopal effect, whereby the immune system can be activated locally in the liver, and then migrate and attack the remote lesions.

For convenience, in this specification the compound of the formula:

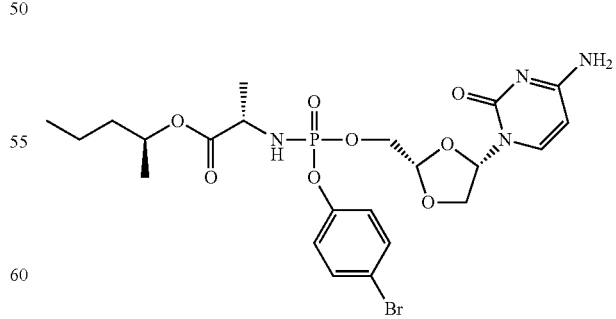

its diastereomers or a pharmaceutically acceptable salt thereof, will generally be referred to interchangeably as "MIV-818". In some of the accompanying Figures, MIV-818 is referred to as MDR_MV087313.

A preferred embodiment of MIV-818 is the diastereomer with the structure:

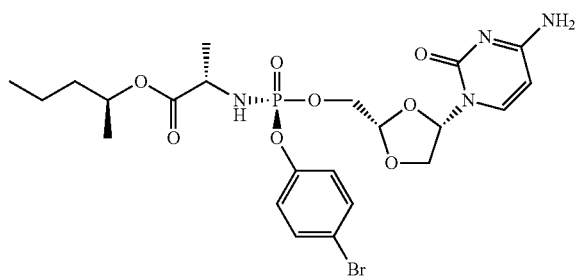 [SMILES: CCC[C@H](C)OC(=O)[C@H](C)N[P@](=O)(OC[C@H]1OC[C@@H](n2ccc(N)nc2=O)O1)Oc1ccc(Br)cc1]

MIV-818 is typically administered orally, is taken into the blood, and via first pass metabolism is concentrated in the liver. MIV-818 is stable in human plasma, but regrettably is very quickly metabolized in rodent blood. This in turn means that essentially all in vivo models generally used in solid tumour oncology are simply not feasible to use, including those intended to assess PK/PD, efficacy, mechanism and synergy of combination therapy with checkpoint inhibitors such as PD-1 antagonists. The elucidation of the present interaction between the orally administered MIV-808 and the parenterally administered PD-1 antagonist has thus been induced, in part, from sophisticated mechanistic models, as outlined in the Examples.

In certain embodiments, the liver cancer or tumour is a primary liver tumour selected from hepatocellular cancer (HCC), hepatoblastoma, cholangiocarcinoma or cholangiocellular cystadenocarcinoma, especially HCC.

In certain embodiments, the liver cancer or tumour is a secondary liver tumour, such as those derived from primary tumours in the gastric tract, breast, ovaries, bronchus or kidney.

In certain embodiments, MIV-818 is formulated in an oral dosage form e.g. a tablet or a capsule. In one embodiment, MIV-818 is administered orally to a mammal in need thereof, typically a human. In one embodiment, MIV-818 is administered to a mammal in need thereof for a sustained period of time. In one embodiment, the MIV-818 is administered to a subject in need thereof cyclically (e.g. dosing for one or more days, followed by a resting period). In one embodiment, the MIV-818 is administered to a mammal in need thereof over multiple dosing cycles.

In certain embodiments, the PD-1 inhibitor is an anti-PD-1 antibody. In one embodiment, the antibody is a monoclonal antibody. In one embodiment, the antibody is a humanized antibody. In a particular embodiment, the anti-PD-1 monoclonal antibody is pembrolizumab.

In certain embodiments, the liver cancer or tumour is relapsed or refractory. In certain embodiments, the mammal having a disease or disorder did not respond to a prior treatment. In certain embodiments, the prior treatment comprises sorafenib, regorafenib or donafenib.

In certain embodiments, the anti-PD1 monoclonal antibody is a humanized monoclonal IgG4 antibody. In one embodiment, the humanized monoclonal IgG4 antibody is pembrolizumab.

In certain embodiments, the anti-PDL1 monoclonal antibody is a humanized monoclonal IgG1 antibody. In one embodiment, the humanized monoclonal IgG1 antibody is durvalumab (MEDI4736).

In one embodiment, the anti-PD1 monoclonal antibody is pembrolizumab, MK-3475, pidilizumab or nivolumab (BMS-936558, MDX-1106, or ONO-4538).

In one embodiment, the anti-PDL1 monoclonal antibody is BMS-936559, atezolizumab (MPDL3280A), or durvalumab (MEDI4736).

In one embodiment the anti-PD-L1 monoclonal antibody is Bavencio (avelumab).

In one embodiment, the anti-PD-1 monoclonal antibody is Camrelizumab (SHR1210).

In one embodiment, the anti-PD-1 monoclonal antibody is Tislelizumab (BGBA317).

In certain embodiments, MIV-818 is administered for 21 consecutive days followed by seven consecutive days of rest in a 28-day cycle. In certain embodiments, MIV-818 is administered for 14 consecutive days followed by seven consecutive days of rest in a 21-day cycle.

In certain embodiments, the anti-PD1/anti-PDL1 monoclonal antibody is administered on days 7 and 21 in a 28-day cycle. In certain embodiments, the anti-PD1/anti-PDL1 monoclonal antibody is administered on days 8 and 21 in a 28 day cycle. In certain embodiments, the anti-PD1/anti-PDL1 monoclonal antibody is administered on day 1 in a 28-day cycle. In certain embodiments, the anti-PD1/anti-PDL1 monoclonal antibody is administered on day 1 in a 21-day cycle.

In certain embodiments, MIV-818 is administered for 21 consecutive days followed by seven consecutive days of rest in a 28-day cycle, and the anti-PD1/anti-PDL1 monoclonal antibody is administered on days 7 and 21 of the 28-day cycle. In certain embodiments, MIV-818 is administered for 21 consecutive days followed by seven consecutive days of rest in a 28-day cycle, and the anti-PD1/anti-PDL1 monoclonal antibody is administered on days 8 and 21 of the 28-day cycle. In certain embodiments, MIV-818 is administered for 21 consecutive days followed by seven consecutive days of rest in a 28-day cycle, and the anti-PD1/anti-PDL1 monoclonal antibody is administered on day 1 of the 28-day cycle.

In a specific embodiment, the liver cancer is HCC. In a more specific embodiment, the HCC is relapsed or refractory. In a particular embodiment, the HCC does not respond, or no longer responds to treatment with sorafenib, regorafenib or donafenib.

In certain embodiments, MIV-818 is administered for 14 consecutive days followed by seven consecutive days of rest in a 21-day cycle, and the anti-PD1/anti-PDL1 monoclonal antibody is administered on day 1 of the 21-day cycle.

In certain embodiments, MIV-818 is orally administered in an amount of about 25 mg, about 50 mg, about 75 mg, about 100 mg, about 150 mg, about 200 mg, about 250 mg, about 300 mg, about 350 mg, about 400 mg, about 500 mg, or about 600 mg. In certain embodiments, MIV-818 is orally administered in an amount of about 50 mg, about 100 mg, about 200 mg, about 300 mg, about 400 mg, about 500 mg, or about 600 mg per day.

In another embodiment, MIV-818 is administered in an amount of about 600 mg per day. In another embodiment, MIV-818 is administered in an amount of about 500 mg per day. In another embodiment, MIV-818 is administered in an amount of about 400 mg per day. In one embodiment, MIV-818 is administered in an amount of about 300 mg per day. In another embodiment, MIV-818 is administered in an amount of about 200 mg per day. In another embodiment, MIV-818 is administered in an amount of about 100 mg per day. In another embodiment, MIV-818 is administered in an amount of about 50 mg per day.

In certain embodiments, MIV-818 is administered once per day. In certain embodiments, MIV-818 is administered twice per day. In one embodiment, MIV-818 is administered in an amount of about 200 mg, about 150 mg, or about 100 mg, twice per day. In one embodiment, MIV-818 is administered in an amount of about 200 mg, twice per day. In one embodiment, MIV-818 is administered in an amount of about 150 mg, twice per day. In one embodiment, MIV-818 is administered in an amount of about 100 mg twice per day.

In certain embodiments, the anti-PD1/anti-PDL1 monoclonal antibody is administered parenterally. In certain embodiments, the anti-PD1/anti-PDL1 monoclonal antibody is administered in an amount of about 0.5 mg/Kg (about 0.5 mg of anti-PD1/anti-PDL1 monoclonal antibody per kilogram of a subject's mass), about 1 mg/Kg, about 2 mg/Kg, about 3 mg/Kg, about 4 mg/Kg, about 5 mg/Kg, about 6 mg/Kg, about 7 mg/Kg, about 8 mg/Kg, about 9 mg/Kg, about 10 mg/Kg, about 11 mg/Kg, about 12 mg/Kg, about 13 mg/Kg, about 14 mg/Kg, about 15 mg/Kg, about 16 mg/Kg, about 17 mg/Kg, about 18 mg/Kg, about 19 mg/Kg, or about 20 mg/Kg.

In a specific embodiment, the anti-PD1/anti-PDL1 monoclonal antibody is administered intravenously in an amount of about 20 mg/Kg per day. In a specific embodiment, the anti-PD1/anti-PDL1 monoclonal antibody is administered intravenously in an amount of about 19 mg/Kg per day. In a specific embodiment, the anti-PD1/anti-PDL1 monoclonal antibody is administered intravenously in an amount of about 18 mg/Kg per day. In a specific embodiment, the anti-PD1/anti-PDL1 monoclonal antibody is administered intravenously in an amount of about 17 mg/Kg per day. In a specific embodiment, the anti-PD1/anti-PDL1 monoclonal antibody is administered intravenously in an amount of about 16 mg/Kg per day. In a specific embodiment, the anti-PD1/anti-PDL1 monoclonal antibody is administered intravenously in an amount of about 15 mg/Kg per day. In a specific embodiment, the anti-PD1/anti-PDL1 monoclonal antibody is administered intravenously in an amount of about 14 mg/Kg per day. In a specific embodiment, the anti-PD1/anti-PDL1 monoclonal antibody is administered intravenously in an amount of about 13 mg/Kg per day. In a specific embodiment, the anti-PD1/anti-PDL1 monoclonal antibody is administered intravenously in an amount of about 12 mg/Kg per day. In a specific embodiment, the anti-PD1/anti-PDL1 monoclonal antibody is administered intravenously in an amount of about 11 mg/Kg per day. In a specific embodiment, the anti-PD1/anti-PDL1 monoclonal antibody is administered intravenously in an amount of about 10 mg/Kg per day. In a specific embodiment, the anti-PD1/anti-PDL1 monoclonal antibody is administered intravenously in an amount of about 9 mg/Kg per day. In a specific embodiment, the anti-PD1/anti-PDL1 monoclonal antibody is administered intravenously in an amount of about 8 mg/Kg per day. In a specific embodiment, the anti-PD1/anti-PDL1 monoclonal antibody is administered intravenously in an amount of about 7 mg/Kg per day. In a specific embodiment, the anti-PD1/anti-PDL1 monoclonal antibody is administered intravenously in an amount of about 6 mg/Kg per day. In a specific embodiment, the anti-PD1 or anti-PDL1 monoclonal antibody is administered intravenously in an amount of about 5 mg/Kg. In a specific embodiment, the anti-PD1/anti-PDL1 monoclonal antibody is administered intravenously in an amount of about 4 mg/Kg per day. In a specific embodiment, the anti-PD1/anti-PDL1 monoclonal antibody is administered intravenously in an amount of about 3 mg/Kg per day. In a specific embodiment, the anti-PD1/anti-PDL1 monoclonal antibody is administered intravenously in an amount of about 2 mg/Kg per day. In a specific embodiment, the anti-PD1/anti-PDL1 monoclonal antibody is administered intravenously in an amount of about 1 mg/Kg per day. In a specific embodiment, the anti-PD1/anti-PDL1 monoclonal antibody is administered intravenously in an amount of about 0.5 mg/Kg per day.

In a specific embodiment, the anti-PD1 or anti-PDL1 monoclonal antibody is administered intravenously in an amount of about 1,500 mg per day. In a specific embodiment, the anti-PD1 or anti-PDL1 monoclonal antibody is administered in an amount of about 1,500 mg per day on day 1 in a 28-day cycle. In a particular embodiment, the anti-PD1/anti-PDL1 monoclonal antibody is administered intravenously in an amount of about 10 mg/Kg per day on day 1 in a 28-day cycle, days 7 and 21 in a 28-day cycle, or on days 8 and 21 in a 28-day cycle. In a particular embodiment, the anti-PD1/anti-PDL1 monoclonal antibody is administered intravenously in an amount of about 10 mg/Kg per day on day 1 in a 28-day cycle. In a particular embodiment, the anti-PD1/anti-PDL1 monoclonal antibody is administered intravenously in an amount of about 10 mg/Kg per day on days 7 and 21 in a 28-day cycle. In a particular embodiment, the anti-PD1/anti-PDL1 monoclonal antibody is administered intravenously in an amount of about 10 mg/Kg per day on days 8 and 21 in a 28-day cycle. In a particular embodiment, the anti-PD1/anti-PDL1 monoclonal antibody is administered intravenously in an amount of about 5 mg/Kg per day on days 7 and 21 in a 28-day cycle.

In one embodiment, the anti-PD1 monoclonal antibody is pembrolizumab and is administered as a 30 minute i.v.infusion.

In one embodiment, the anti-PD1 monoclonal antibody is MK-3475 and is administered as a 30 minute i.v.infusion.

In one embodiment, the anti-PD1 monoclonal antibody is pidilizumab and is administered as a 30 minute i.v.infusion.

In one embodiment, the anti-PD1 monoclonal antibody is nivolumab (BMS-936558, MDX-1106, or ONO-4538) and is administered as a 30 minute i.v.infusion.

In one embodiment, the anti-PDL1 monoclonal antibody is atezolizumab (MPDL3280A) and is administered as a 30 minute i.v infusion.

In one embodiment, the anti-PDL1 monoclonal antibody is durvalumab (MEDI4736) and is administered as a 30 minute i.v.infusion.

In one embodiment, durvalumab (MEDI4736) is administered on Day 1 of each 28-day treatment cycle as a single 1500 mg IV infusion.

In certain embodiments, MIV-818 is in the form of a solid dosage unit, such as a capsule, tablet or caplet.

In certain embodiments, the method further comprises administering a therapeutically effective amount of an additional active agent, such as sorafenib, regorafenib or donafenib, sequentially or concurrently with MIV-818 and the PD-1 antagonist.

In a specific embodiment, the subject is a human.

IV. BRIEF DESCRIPTION OF THE DRAWINGS

Aspects of the invention are illustrated by reference to the Examples below and the accompanying drawings in which.

Figure 14:
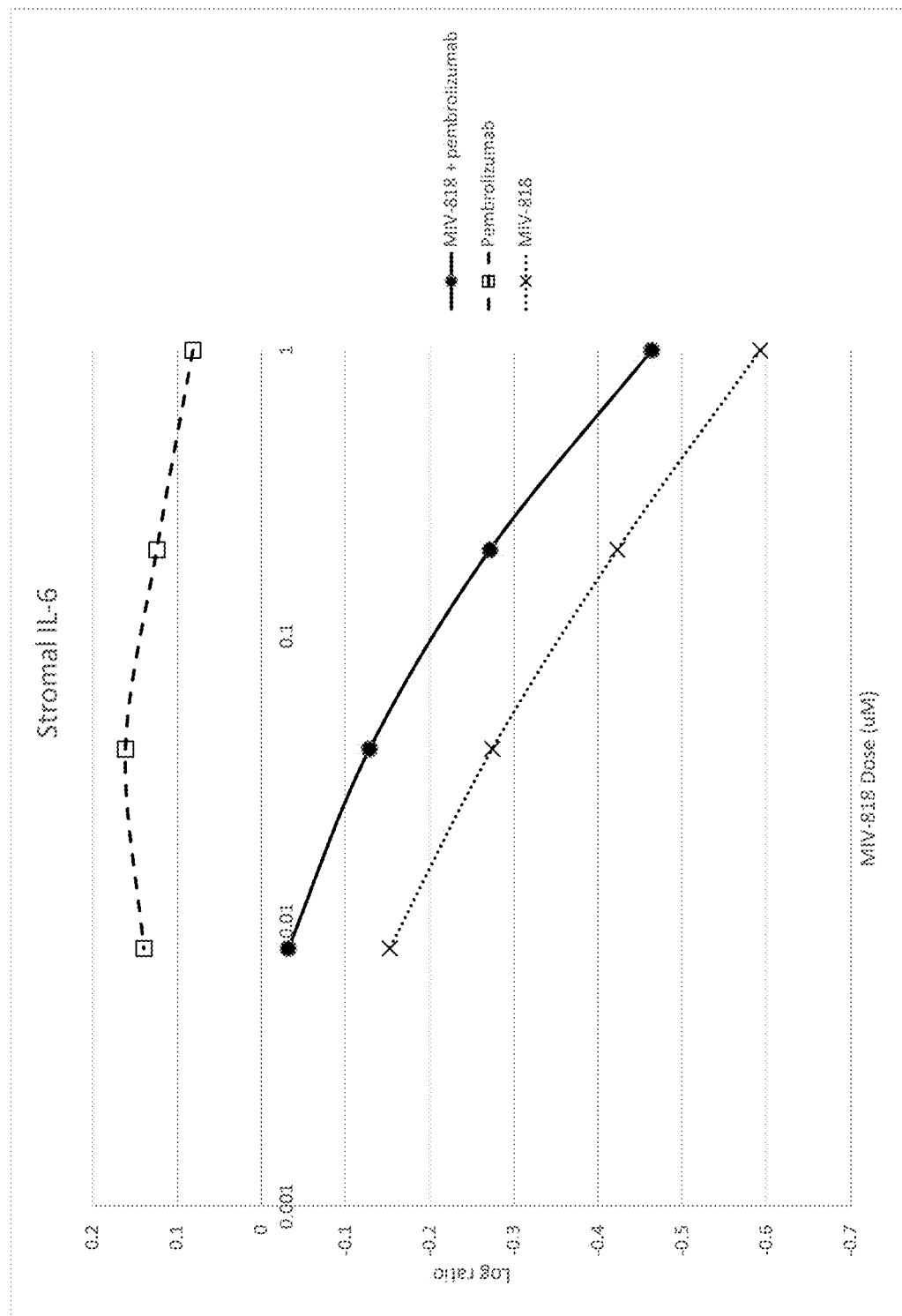
FIG. 14 is a plot showing the relationship between dose and effects of the components MIV-818 and pembrolizumab on stromal IL-6 in the cell culture model of the tumour microenvironment.
Figure 15:
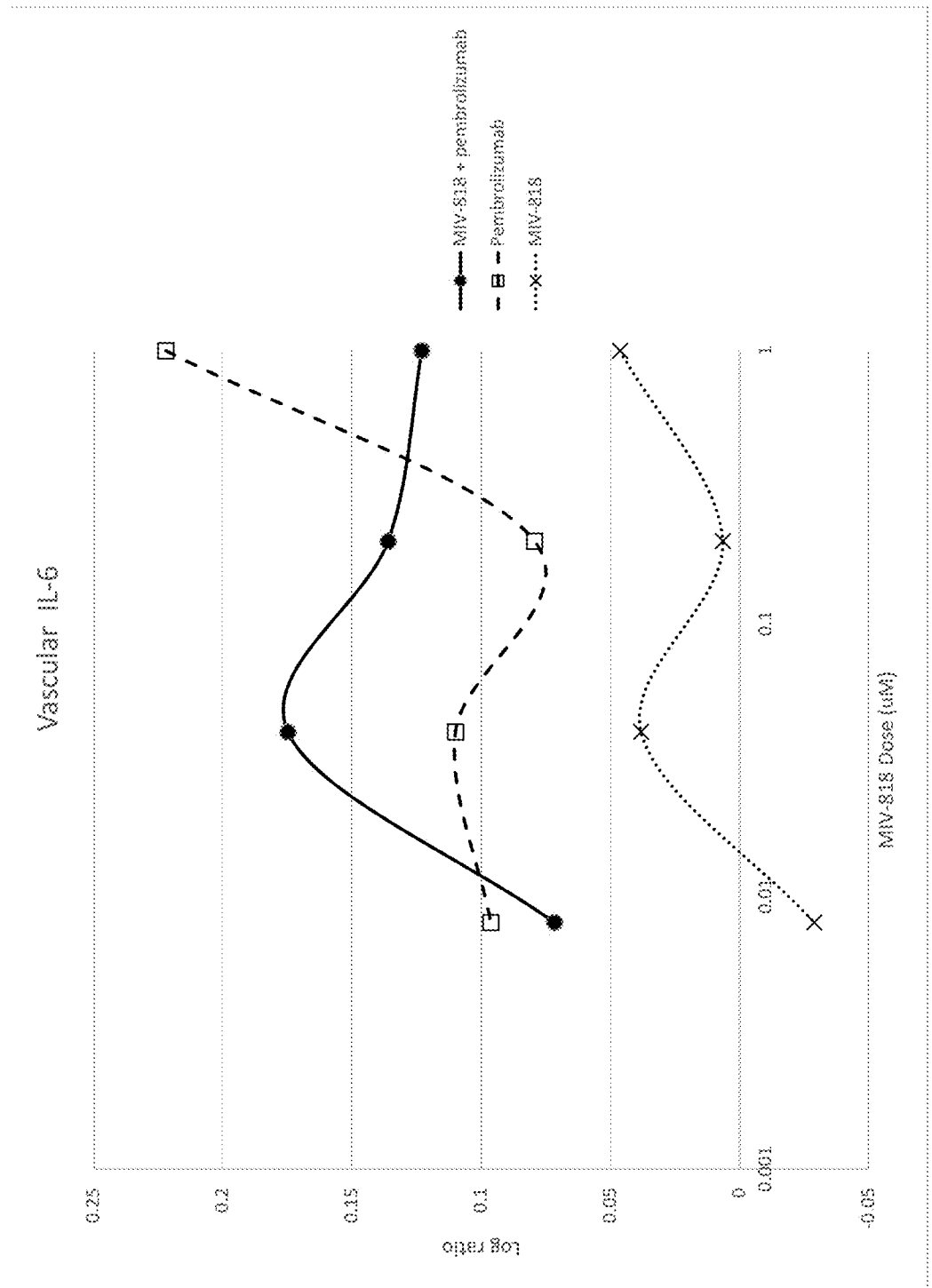
Figure 16:
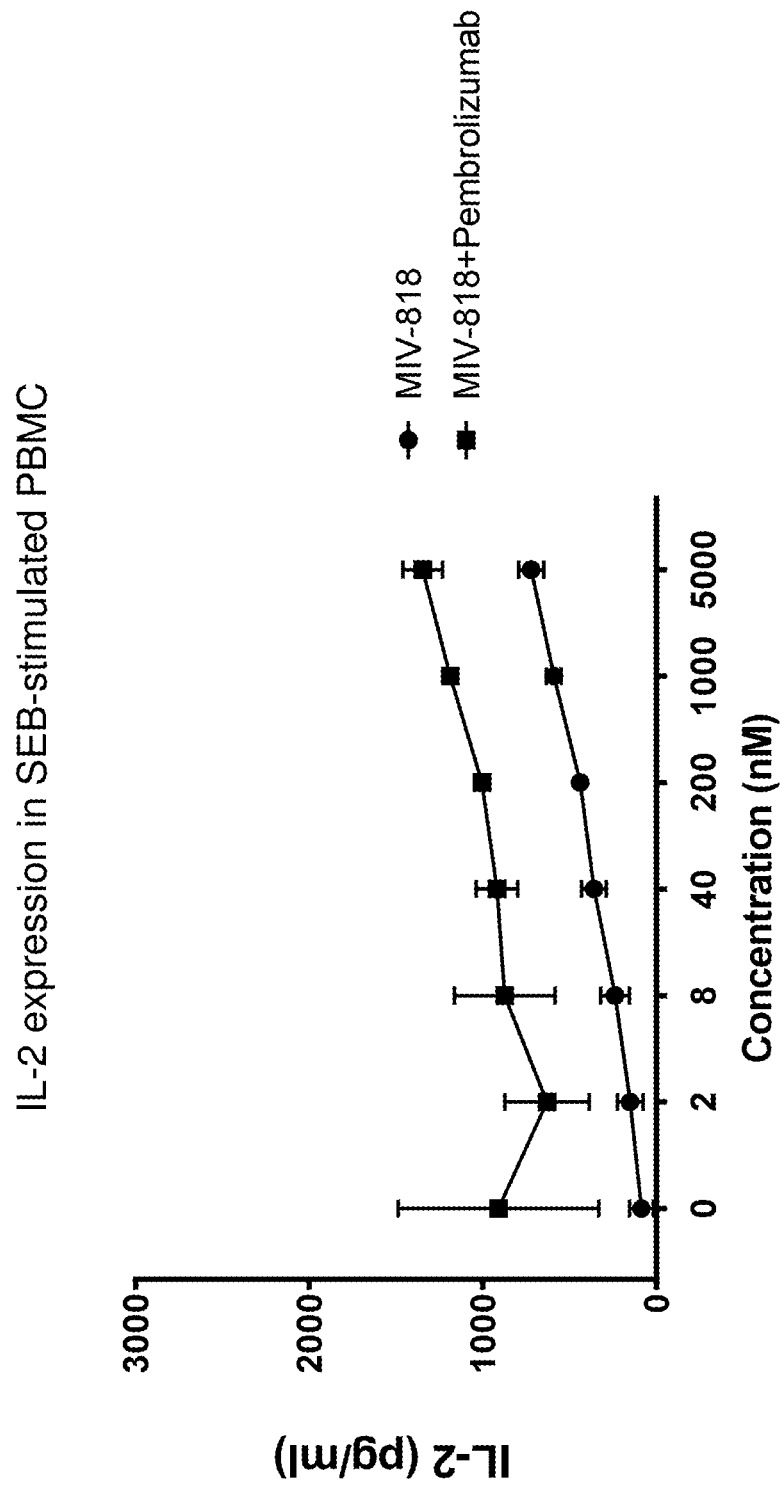
Figure 17:
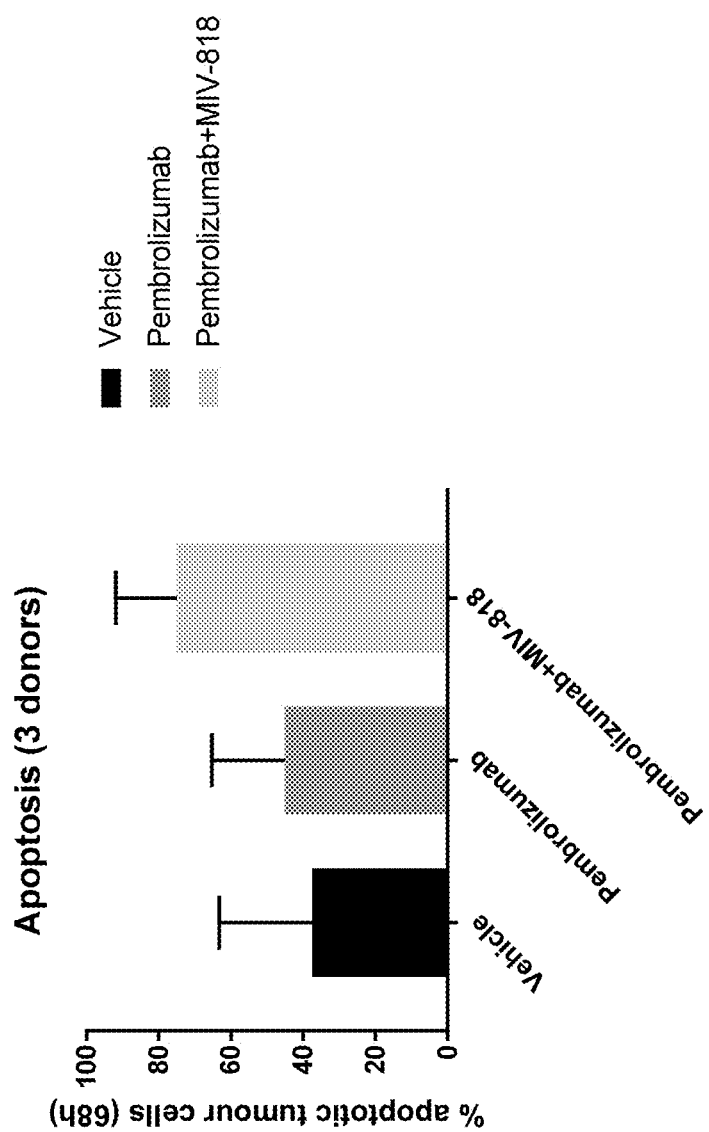
Figure 18:
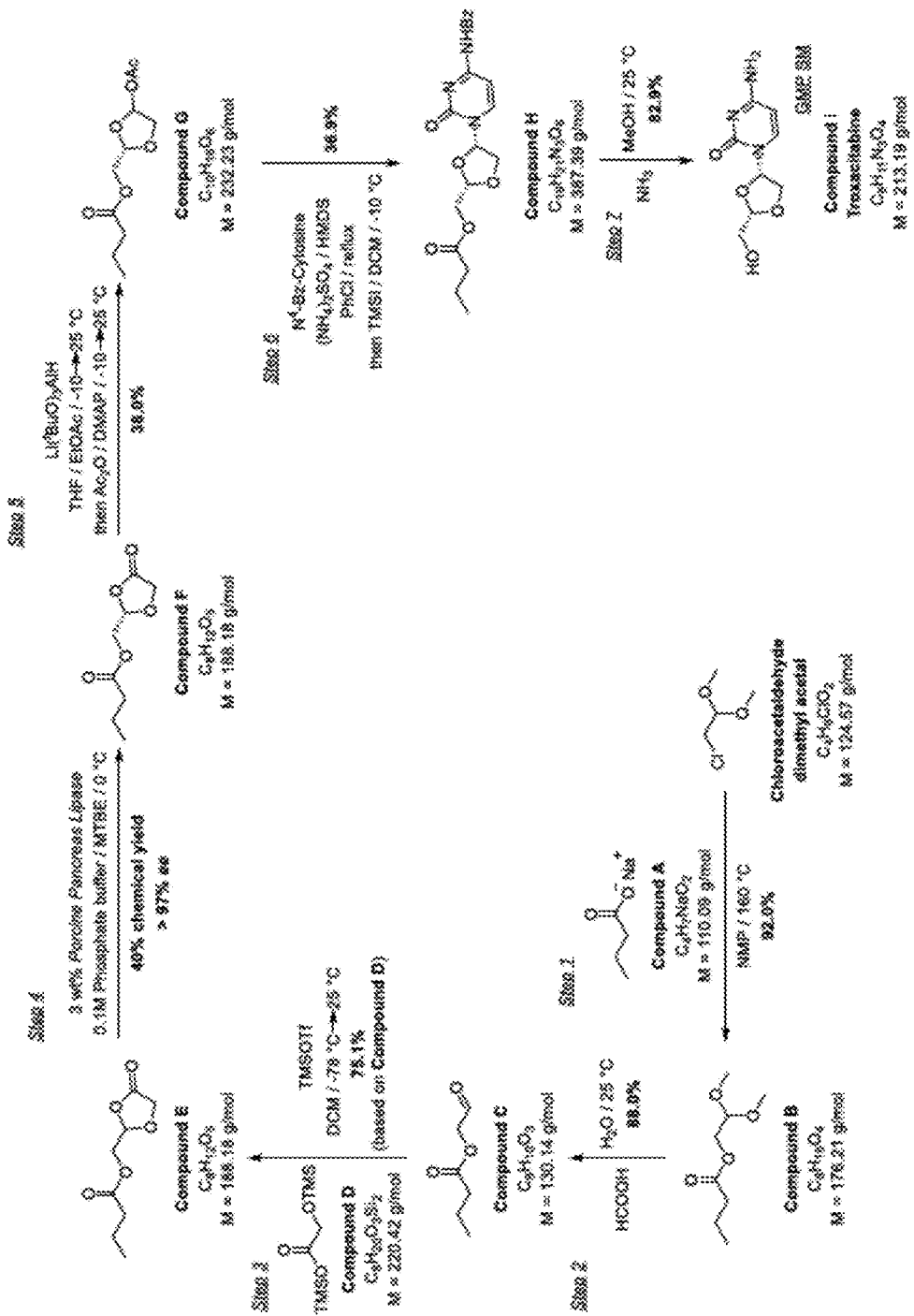
Figure 19:
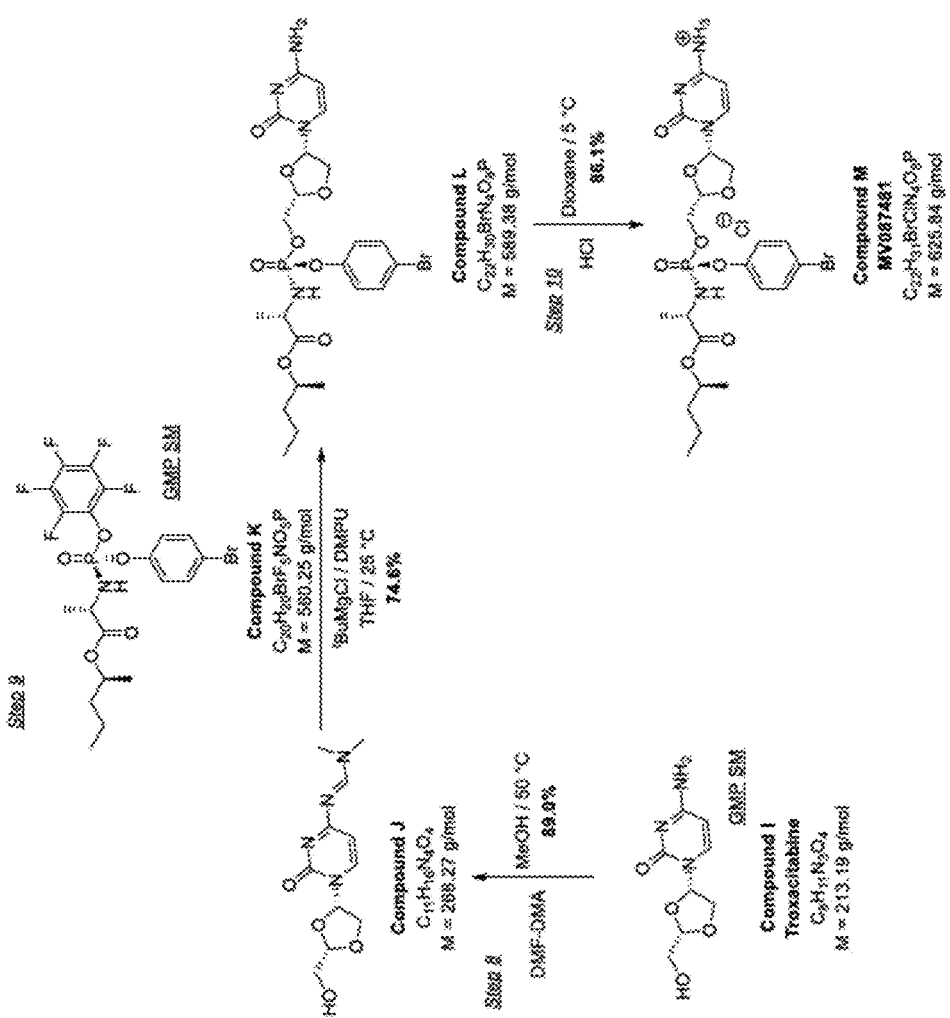

FIG. 15 a plot corresponding to FIG. 14, but showing that vascular IL6 is substantially unaffected by the combination;

FIG. 16 a graph showing enhanced IL-2 expression by MIV-818 in a dose-dependent manner, and the enhancement in combination with pembrolizumab;

FIG. 17 a graph showing the increased PBMC-mediated tumour cell killing by the combination of MIV-818 and pembrolizumab;

FIG. 18 is a scheme showing the synthesis of the nucleoside precursor;

FIG. 19 is a scheme showing the coupling of a phosphoramide reagent with the nucleoside precursor.

V. DETAILED DESCRIPTION

Unless defined otherwise, all technical and scientific terms used herein have the same meaning as commonly understood by one of ordinary skill in the art. All publications and patents referred to herein are incorporated by reference herein in their entireties.

A. Definitions

As used in the specification and the accompanying claims, the indefinite articles "a" and "an" and the definite article "the" include plural as well as singular referents, unless the context clearly dictates otherwise.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 30%, 25%, 20%, 15%, 10%, 9%, 8%, 7%, 6%, 5%, 4%, 3%, 2%, 1%, 0.5%, 0.1%, or 0.05% of a given value or range.

As used herein, and unless otherwise specified, the terms "treat", "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound or dosage form provided herein, with or without one or more additional active agent(s), after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound or dosage form provided herein, with or without one or more other additional active agent(s), prior to the onset of symptoms, particularly to subjects at risk of disease or disorders provided herein. The terms encompass the inhibition or reduction of a symptom of the particular disease. Subjects with familial history of a disease in particular are candidates for preventive regimens in certain embodiments. In addition, subjects who have a history of recurring symptoms are also potential candidates for prevention. In this regard, the term "prevention" may be interchangeably used with the term "prophylactic treatment."

As used herein, and unless otherwise specified, the terms "manage", "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a subject who had suffered from the particular disease in an attempt to prevent or minimize the recurrence of the disease.

As used herein, amelioration of the symptoms of a particular disorder by administration of a particular pharmaceutical composition refers to any lessening, whether permanent or temporary, lasting or transient, that can be attributed to or associated with administration of the composition.

As used herein, and unless otherwise specified, the terms "therapeutically effective amount" and "effective amount" of a compound mean an amount sufficient to provide a therapeutic benefit in the treatment or management of a disease or disorder, or to delay or minimize one or more symptoms associated with the disease or disorder. A "therapeutically effective amount" and "effective amount" of a compound mean an amount of therapeutic agent, alone or in combination with one or more other agent(s), which provides a therapeutic benefit in the treatment or management of the disease or disorder. The terms "therapeutically effective amount" and "effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with one or more other agent(s), which provides a prophylactic benefit in the prevention of the disease. The term "prophylactically effective amount" can encompass an amount that improves overall prophylaxis or enhances the prophylactic efficacy of another prophylactic agent.

"Tumour," as used herein, refers to neoplastic cell growth and proliferation, whether malignant or benign, and all pre-cancerous and cancerous cells and tissues.

"Neoplastic," as used herein, refers to any form of dysregulated or unregulated cell growth, whether malignant or benign, resulting in abnormal tissue growth. Thus, "neoplastic cells" include malignant and benign cells having dysregulated or unregulated cell growth.

The terms "cancer" and "cancerous" refer to or describe the physiological condition in mammals that is typically characterized by unregulated cell growth. Examples of cancer include solid tumours, such as HCC.

As used herein, and unless otherwise specified, the term "proliferative" disorder or disease refers to unwanted cell proliferation of one or more subset of cells in a multicellular organism resulting in harm (i.e., discomfort or decreased life expectancy) to the multicellular organism. For example, as used herein, proliferative disorder or disease includes neoplastic disorders and other proliferative disorders.

As used herein, and unless otherwise specified, the term "relapsed" refers to a situation where a subject, that has had a remission of cancer after a therapy, has a return of cancer cells.

As used herein, and unless otherwise specified, the term "refractory" or "resistant" refers to a circumstance where a subject, even after intensive treatment, has residual cancer cells in the body.

The terms "composition", "formulation," and "dosage form," as used herein are intended to encompass compositions comprising the specified ingredient(s) (in the specified amounts, if indicated), as well as any product(s) which result, directly or indirectly, from combination of the specified ingredient(s) in the specified amount(s). By "pharmaceutical" or "pharmaceutically acceptable" it is meant that any diluent(s), excipient(s) or carrier(s) in the composition, formulation, or dosage form are compatible with the other ingredient(s) and not deleterious to the recipient thereof. Unless indicated otherwise, the terms "composition", "formulation", and "dosage form" are used herein interchangeably.

The term "immediate release," when used herein in reference to a composition, formulation, or dosage form provided herein, means that the composition, formulation, or dosage form does not comprise a component (e.g., a coating) that serves to delay the spatial and/or temporal release of some or all of the API from the composition, formulation, or dosage form beyond the stomach following oral administration. In certain embodiments, an immediate release composition, formulation, or dosage form is one that releases the API substantially in the stomach following oral administration. In specific embodiments, an immediate release composition, formulation, or dosage form is one that is not delayed-release. In specific embodiments, an immediate release composition, formulation, or dosage form is one that does not comprise an enteric coating.

The term "subject" means mammals, including, but not limited to, primates (e.g., humans), cows, sheep, goats, horses, dogs, cats, rabbits, rats, mice and the like. In specific embodiments, the subject is a human.

The terms "co-administration" and "in combination with" include the administration of two or more therapeutic agents either simultaneously, concurrently or sequentially within no specific time limits. In one embodiment, the agents are present in the cell or in the subject's body at the same time or exert their biological or therapeutic effect at the same time. In one embodiment, the therapeutic agents are in the same composition or unit dosage form. In other embodiments, the therapeutic agents are in separate compositions or unit dosage forms. In certain embodiments, a first agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

The term "isotopic composition" refers to the amount of each isotope present in a given atomic position, and "natural isotopic composition" refers to the naturally occurring isotopic composition or abundance for a given atomic position. Atomic positions containing their natural isotopic composition may also be referred to herein as "non-enriched." Unless otherwise designated, the atomic positions of the compounds recited herein are meant to represent any stable isotope of that atom. For example, unless otherwise stated, when a position is designated specifically as "H" or "hydrogen," the position is understood to have hydrogen at its natural isotopic composition.

The term "isotopically enriched" refers to an atomic position having an isotopic composition other than the natural isotopic composition of that atom. "Isotopically enriched" may also refer to a compound containing at least one atomic position having an isotopic composition other than the natural isotopic composition of that atom. As used herein, an "isotopologue" is an isotopically enriched compound.

The term "isotopic enrichment" refers to the percentage of incorporation of an amount of a specific isotope at a given atomic position in a molecule in the place of that atom's natural isotopic composition. For example, deuterium enrichment of 1% at a given position means that 1% of the molecules in a given sample contain deuterium at the specified position. Because the naturally occurring distribution of deuterium is about 0.0156%, deuterium enrichment at any position in a compound synthesized using non-enriched starting materials is about 0.0156%.

The term "isotopic enrichment factor" refers to the ratio between the isotopic composition and the natural isotopic composition of a specified isotope.

With regard to the compounds provided herein, when a particular atomic position is designated as having deuterium or "D," it is understood that the abundance of deuterium at that position is substantially greater than the natural abundance of deuterium, which is about 0.015%. A position designated as having deuterium typically has a minimum isotopic enrichment factor of, in particular embodiments, at least 1000 (15% deuterium incorporation), at least 2000

(30% deuterium incorporation), at least 3000 (45% deuterium incorporation), at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation) at each designated deuterium position.

The isotopic enrichment and isotopic enrichment factor of the compounds provided herein can be determined using conventional analytical methods known to one of ordinary skill in the art, including, e.g., mass spectrometry, nuclear magnetic resonance spectroscopy, and crystallography.

B. MIV-818

The synthesis of MIV-818 is shown in WO2016/030335. In short, the nucleoside precursor is prepared as shown in FIG. 18, and coupled to the phosphoramide reagent as shown in FIG. 19.

MIV-818 is typically >75%, such as >90%, preferably >95%, and more preferably at least 95% ee of the diastereomer:

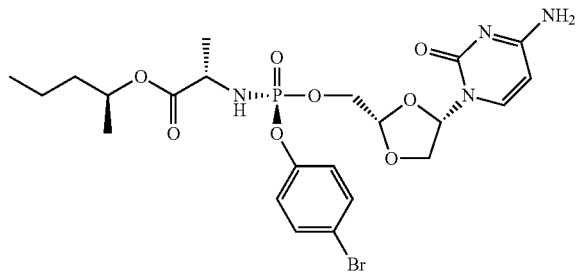 [SMILES: CCC[C@H](C)OC(=O)[C@H](C)N[P@](=O)(OC[C@H]1OC[C@@H](n2ccc(N)nc2=O)O1)Oc1ccc(Br)cc1]

Alternatively, the racemate at the phosphorous may be used, and will typically be cheaper to manufacture.

C. Pharmaceutical Formulations

1. Overview

Embodiments herein encompass pharmaceutical formulations and compositions comprising MIV-818, wherein the formulations and compositions are prepared for oral administration. Particular embodiments relate to the use of MIV-818 for the preparation of pharmaceutical formulations and compositions for treating particular medical indications, as provided herein. The pharmaceutical formulations and compositions comprising MIV-818 provided herein are intended for oral delivery of the in subjects in need thereof. Oral delivery formats include, but are not limited to, tablets, capsules, caplets, solutions, suspensions, and syrups, and may also comprise a plurality of granules, beads, powders or pellets that may or may not be encapsulated. Such formats may also be referred to herein as the "drug core" which contains the MIV-818.

Particular embodiments herein provide solid oral dosage forms that are tablets or capsules. In certain embodiments, the formulation is a tablet comprising MIV-818. In certain embodiments, the formulation is a capsule comprising MIV-818. In certain embodiments, the tablets or capsules provided herein optionally comprise one or more excipients, such as, for example, glidants, diluents, lubricants, colorants, disintegrants, granulating agents, binding agents, polymers, and coating agents. In certain embodiments, the formulation is an immediate release tablet. In certain embodiments, the formulation is a controlled release tablet releasing the API, e.g., substantially in the intestinal, tract. In certain embodiments, the formulation is a hard gelatin capsule. In certain embodiments, the formulation is a soft gelatin capsule. In certain embodiments, the capsule is a hydroxypropyl methylcellulose (HPMC) capsule. In certain embodiments, the formulation is an immediate release capsule. In certain embodiments, the formulation is an immediate or controlled release capsule releasing the API, e.g., substantially in the intestinal tract.

In particular embodiments, the formulations may be prepared using conventional methods known to those skilled in the field of pharmaceutical formulation, as described, e.g., in pertinent textbooks. See, e.g., REMINGTON, THE SCIENCE AND PRACTICE OF PHARMACY, 20th Edition, Lippincott Williams & Wilkins, (2000); ANSEL et al., PHARMACEUTICAL DOSAGE FORMS AND DRUG DELIVERY SYSTEMS, 7th Edition, Lippincott Williams & Wilkins, (1999); GIBSON, PHARMACEUTICAL PRE-FORMULATION AND FORMULATION, CRC Press (2001).

In particular embodiments, the specific amount of MIV-818 in the formulation is, e.g., about 10 mg, about 20 mg, about 40 mg, about 60 mg, about 80 mg, about 100 mg, about 120 mg, about 140 mg, about 160 mg, about 180 mg, about 200 mg, about 220 mg, least about 240 mg, about 260 mg, about 280 mg, about 300 mg, about 320 mg, about 340 mg, about 360 mg, about 380 mg, about 400 mg, about 420 mg, about 440 mg, about 460 mg, about 480 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500 mg, about 3000 mg, about 4000 mg, or about 5000 mg.

In particular embodiments, the specific amount of MIV-818 in the formulation is, e.g., at least about 10 mg, at least about 20 mg, at least about 40 mg, at least about 60 mg, at least about 80 mg, at least about 100 mg, at least about 120 mg, at least about 140 mg, at least about 160 mg, at least about 180 mg, at least about 200 mg, at least about 220 mg, at least about 240 mg, at least about 260 mg, at least about 280 mg, at least about 300 mg, at least about 320 mg, at least about 340 mg, at least about 360 mg, at least about 380 mg, at least about 400 mg, at least about 420 mg, at least about 440 mg, at least about 460 mg, at least about 480 mg, at least about 500 mg, at least about 600 mg, at least about 700 mg, at least about 800 mg, at least about 900 mg, at least about 1000 mg, at least about 1100 mg, at least about 1200 mg, at least about 1300 mg, at least about 1400 mg, at least about 1500 mg, at least about 1600 mg, at least about 1700 mg, at least about 1800 mg, at least about 1900 mg, at least about 2000 mg, at least about 2100 mg, at least about 2200 mg, at least about 2300 mg, at least about 2400 mg, at least about 2500 mg, at least about 3000 mg, at least about 4000 mg, or at least about 5000 mg.

In certain embodiments, the formulation is a tablet, wherein the tablet is manufactured using standard, art-recognized tablet processing procedures and equipment. In certain embodiments, the method for forming the tablets is direct compression of a powdered, crystalline and/or granular composition comprising MIV-818, alone or in combination with one or more excipients, such as, for example, carriers, additives, polymers, or the like. In certain embodiments, as an alternative to direct compression, the tablets may be prepared using wet granulation or dry granulation processes. In certain embodiments, the tablets are molded rather than compressed, starting with a moist or otherwise tractable material. In certain embodiments, compression and granulation techniques are used.

In certain embodiments, the formulation is a capsule, wherein the capsules may be manufactured using standard, art-recognized capsule processing procedures and equipment. In certain embodiments, soft gelatin capsules may be prepared in which the capsules contain a mixture of MIV-818 and vegetable oil or non-aqueous, water miscible materials such as, for example, polyethylene glycol and the like. In certain embodiments, hard gelatin capsules may be prepared containing granules of MIV-818 in combination with a solid pulverulent carrier, such as, for example, lactose, saccharose, sorbitol, mannitol, potato starch, corn starch, amylopectin, cellulose derivatives, or gelatin. In certain embodiments, a hard gelatin capsule shell may be prepared from a capsule composition comprising gelatin and a small amount of plasticizer such as glycerol. In certain embodiments, as an alternative to gelatin, the capsule shell may be made of a carbohydrate material. In certain embodiments, the capsule composition may additionally include polymers, colorings, flavorings and opacifiers as required. In certain embodiments, the capsule comprises HPMC.

In certain embodiments, the pharmaceutical formulation provided herein is a compressed tablet comprising MIV-818. In addition to the MIV-818, the tablet optionally comprises one or more excipients, including (a) diluents or fillers, which may add necessary bulk to a formulation to prepare tablets of the desired size; (b) binders or adhesives, which may promote adhesion of the particles of the formulation, enabling a granulation to be prepared and maintaining the integrity of the final tablet; (c) disintegrants or disintegrating agents, which, after administration, may promote breakup of the tablets to smaller particles for improved drug availability; (d) anti-adherents, glidants, lubricants or lubricating agents, which may enhance flow of the tableting material into the tablet dies, minimize wear of the punches and dies, prevent the sticking of fill material to the punches and dies, and produce tablets having a sheen; and (e) miscellaneous adjuncts such as colorants and flavorants. After compression, tablets provided herein may be coated with various materials as described herein.

In certain embodiments, the pharmaceutical formulation provided herein is a multiple compressed tablet of MIV-818. Multiple compressed tablets are prepared by subjecting the fill material to more than a single compression. The result may be a multiple-layered tablet or a tablet-within-a-tablet, the inner tablet being the core comprising MIV-818 and optionally one or more excipients, and the outer portion being the shell, wherein the shell comprises one or more excipients, and may or may not contain further MIV-818. Layered tablets may be prepared by the initial compaction of a portion of fill material in a die followed by additional fill material and compression to form two- or three-layered tablets, depending upon the number of separate fills. Each layer may contain a different therapeutic agent, separate from one another for reasons of chemical or physical incompatibility, or the same therapeutic agent for staged drug release, or simply for the unique appearance of the multiple-layered tablet. Each portion of fill may be colored differently to prepare a distinctive looking tablet. In the preparation of tablets having a compressed tablet as the inner core, special machines may be used to place the preformed tablet precisely within the die for the subsequent compression of surrounding fill material.

In certain embodiments, the compressed tablet of MIV-818 may be coated with a colored or an uncolored sugar layer. The coating may be water-soluble and quickly dissolved after oral ingestion. The sugar coating may serve the purpose of protecting the enclosed drug from the environment and providing a barrier to an objectionable taste or smell. The sugar coating may also enhance the appearance of the compressed tablet and permit the imprinting of identifying manufacturer's information.

In certain embodiments, sugar-coated tablets may be 50% larger and heavier than the original uncoated tablets. The sugar-coating of tablets may be divided into the following optional steps: (1) waterproofing and sealing (if needed); (2) sub-coating; (3) smoothing and final rounding; (4) finishing and coloring (if desired); (5) imprinting (if needed); and (6) polishing.

In certain embodiments, the compressed tablet of MIV-818 may be film-coated. Film-coated tablets may be compressed tablets coated with a thin layer of a polymer capable of forming a skin-like film over the tablet. The film is usually colored and has the advantage to be more durable, less bulky, and less time-consuming to apply. By its composition, the coating may be designed to rupture and expose the core tablet at the desired location within the gastrointestinal tract. The film-coating process, which places a thin skin-tight coating of a plastic-like material over the compressed tablet, may produce coated tablets having essentially the same weight, shape, and size as the originally compressed tablet. The film-coating may be colored to make the tablets attractive and distinctive. Film-coating solutions may be non-aqueous or aqueous. In particular embodiments, the non-aqueous solutions may optionally contain one or more of the following types of materials to provide the desired coating to the tablets: (1) a film former capable of producing smooth, thin films reproducible under conventional coating conditions and applicable to a variety of tablet shapes, such as, for example, cellulose acetate phthalate; (2) an alloying substance providing water solubility or permeability to the film to ensure penetration by body fluids and therapeutic availability of the drug, such as, for example, polyethylene glycol; (3) a plasticizer to produce flexibility and elasticity of the coating and thus provide durability, such as, for example, castor oil; (4) a surfactant to enhance spreadability of the film during application, such as, for example, polyoxyethylene sorbitan derivatives; (5) opaquants and colorants to make the appearance of the coated tablets attractive and distinctive, such as, for example, titanium dioxide as an opaquant, and FD&C or D&C dyes as a colorant; (6) sweeteners, flavors, or aromas to enhance the acceptability of the tablet to the subject, such as, for example, saccharin as sweeteners, and vanillin as flavors and aromas; (7) a glossant to provide a luster to the tablets without a separate polishing operation, such as, for example, beeswax; and (8) a volatile solvent to allow the spread of the other components over the tablets while allowing rapid evaporation to permit an effective yet speedy operation, such as, for example, alcohol-acetone mixture. In certain embodiments, an aqueous film-coating formulation may contain one or more of the following: (1) film-forming polymer, such as, for example, cellulose ether polymers as hydroxypropyl methyl-cellulose, hydroxypropyl cellulose, and methyl-cellulose; (2) plasticizer, such as, for example, glycerin, propylene glycol, polyethylene glycol, diethyl phthalate, and dibutyl subacetate; (3) colorant and opacifier, such as, example, FD&C or D&C lakes and iron oxide pigments; or (4) vehicle, such as, for example, water.

In certain embodiments, the compressed tablet of MIV-818 may be compression-coated. The coating material, in the form of a granulation or powder, may be compressed onto a tablet core of drug with a special tablet press.

In certain embodiments, the pharmaceutical formulation is a gelatin-coated tablet of MIV-818. A gelatin-coated tablet is a capsule-shaped compressed tablet that allows the coated product to be smaller than a capsule filled with an equivalent amount of powder. The gelatin coating facilitates swallowing and compared to unsealed capsules, gelatin-coated tablets may be more tamper-evident.

In certain embodiments, compressed tablets may be prepared by wet granulation. Wet granulation is a widely employed method for the production of compressed tablets, and, in particular embodiments, requires one or more the following steps: (1) weighing and blending the ingredients; (2) preparing a damp mass; (3) screening the damp mass into pellets or granules; (4) drying the granulation; (5) sizing the granulation by dry screening; (6) adding lubricant and blending; and (7) tableting by compression.

In certain embodiments, compressed tablets may be prepared by dry granulation. By the dry granulation method, the powder mixture is compacted in large pieces and subsequently broken down or sized into granules. But this method, either the active ingredient or the diluent has cohesive property. After weighing and mixing the ingredients, the powder mixture may be slugged or compressed into large flat tablets or pellets. The slugs then are broken up by hand or by a mill and passed through a screen of desired mesh for sizing. Lubricant is added in the usual manner, and tablets are prepared by compression. Alternatively, instead of slugging, powder compactors may be used to increase the density of a powder by pressing it between high-pressure rollers. The compressed material then is broken up, sized, and lubricated, and tablets are prepared by compression in the usual manner. The roller compaction method is often preferred over slugging. Binding agents used in roller compaction formulations include methylcellulose or hydroxylmethylcellulose and can produce good tablet hardness and friability.

In certain embodiments, compressed tablets may be prepared by direct compression. Some granular chemicals possess free flowing and cohesive properties that enable them to be compressed directly in a tablet machine without the need of wet or dry granulation. For chemicals that do not possess this quality, special pharmaceutical excipients may be used which impart the necessary qualities for the production of tablets by direct compression. Particular tableting excipients include, e.g.

fillers, such as spray-dried lactose, micro-crystals of alpha-monohydrate lactose, sucrose-invert sugar-corn starch mixtures, micro-crystalline cellulose, crystalline maltose, and di-calcium phosphate;
  disintegrating agents, such as direct-compression starch, sodium carboxymethyl starch, cross-linked carboxymethylcellulose fibers, and cross-linked polyvinylpyrrolidone;
  lubricants, such as magnesium searate and talc; and
  glidants, such as fumed silicon dioxide.

In certain embodiments, tablets provided herein may be prepared by moulding. The base for moulded tablets is generally a mixture of finely powdered lactose with or without a portion of powdered sucrose. In preparing the fill, the drug is mixed uniformly with the base by geometric dilution. The powder mixture may be wetted with a mixture of water and alcohol sufficient only to dampen the powder so that it may be compacted. The solvent action of the water on a portion of the lactose/sucrose base effects the biding of the powder mixture upon drying. The alcohol portion hastens the drying process.

In certain embodiments, the pharmaceutical formulations provided herein contain MIV-818 and, optionally, one or more excipients to form a "drug core." Optional excipients include, e.g., diluents (bulking agents), lubricants, disintegrants, fillers, stabilizers, surfactants, preservatives, coloring agents, flavoring agents, binding agents, excipient supports, glidants, permeation enhancement excipients, plasticizers and the like, e.g., as known in the art. It will be understood by those in the art that some substances serve more than one purpose in a pharmaceutical composition. For instance, some substances are binders that help hold a tablet together after compression, yet are also disintegrants that help break the tablet apart once it reaches the target delivery site. Selection of excipients and amounts to use may be readily determined by the formulation scientist based upon experience and consideration of standard procedures and reference works available in the art.

In certain embodiments, formulations provided herein comprise one or more binders. Binders may be used, e.g., to impart cohesive qualities to a tablet, and thus ensure that the tablet remains intact after compression. Suitable binders include, but are not limited to, starch (including corn starch and pregelatinized starch), gelatin, sugars (including sucrose, glucose, dextrose and lactose), polyethylene glycol, propylene glycol, waxes, and natural and synthetic gums, e.g., acacia sodium alginate, polyvinylpyrrolidone, cellulosic polymers (including hydroxypropyl cellulose, hydroxypropylmethylcellulose, methyl cellulose, ethyl cellulose, hydroxyethyl cellulose, carboxymethyl cellulose and the like), veegum, carbomer (e.g., carbopol), sodium, dextrin, guar gum, hydrogenated vegetable oil, magnesium aluminum silicate, maltodextrin, polymethacrylates, povidone (e.g., KOLLIDON, PLASDONE), microcrystalline cellulose, among others. Binding agents also include, e.g., acacia, agar, alginic acid, cabomers, carrageenan, cellulose acetate phthalate, ceratonia, chitosan, confectioner's sugar, copovidone, dextrates, dextrin, dextrose, ethylcellulose, gelatin, glyceryl behenate, guar gum, hydroxyethyl cellulose, hydroxyethylmethyl cellulose, hydroxypropyl cellulose, hydroxypropyl starch, hypromellose, inulin, lactose, magnesium aluminum silicate, maltodextrin, maltose, methylcellulose, poloxamer, polycarbophil, polydextrose, polyethylene oxide, polymethylacrylates, povidone, sodium alginate, sodium carboxymethylcellulose, starch, pregelatinized starch, stearic acid, sucrose, and zein.

The binding agent can be, relative to the drug core, in the amount of about 2% w/w of the drug core; about 4% w/w of the drug core, about 6% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, about 34% w/w of the drug core, about 36% w/w of the drug core, about 38% w/w of the drug core, about 40% w/w of the drug core, about 42% w/w of the drug core, about 44% w/w of the drug core, about 46% w/w of the drug core, about 48% w/w of the drug core, about 50% w/w of the drug core, about 52% w/w of the drug core, about 54% w/w of the drug core, about 56% w/w of the drug core, about 58% w/w of the drug core, about 60% w/w of the drug core, about 62% w/w of the drug core, about 64% w/w of the drug core, about 66% w/w of the drug core; about 68% w/w of the drug core, about 70% w/w of the drug core, about 72% w/w of the drug core, about 74% w/w of the drug core, about 76% w/w of the drug core, about 78% w/w of the drug core, about 80% w/w of the drug core, about 82% w/w of the drug core, about 84% w/w of the drug core, about 86% w/w of the drug core, about 88% w/w of the drug core, about 90% w/w of the drug core, about 92% w/w of the drug core, about 94% w/w of the drug core, about 96% w/w of the drug core, about 98% w/w of the drug core, or more, if determined to be appropriate. In certain embodiments, a suitable amount of a particular binder is determined by one of ordinary skill in the art.

In certain embodiments, formulations provided herein comprise one or more diluents. Diluents may be used, e.g., to increase bulk so that a practical size tablet is ultimately provided. Suitable diluents include dicalcium phosphate, calcium sulfate, lactose, cellulose, kaolin, mannitol, sodium chloride, dry starch, microcrystalline cellulose (e.g., AVICEL), microfine cellulose, pregelitinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT), potassium chloride, sodium chloride, sorbitol and talc, among others. Diluents also include, e.g., ammonium alginate, calcium carbonate, calcium phosphate, calcium sulfate, cellulose acetate, compressible sugar, confectioner's sugar, dextrates, dextrin, dextrose, erythritol, ethylcellulose, fructose, fumaric acid, glyceryl palmitostearate, isomalt, kaolin, lacitol, lactose, mannitol, magnesium carbonate, magnesium oxide, maltodextrin, maltose, medium-chain triglycerides, microcrystalline cellulose, microcrystalline silicified cellulose, powered cellulose, polydextrose, polymethacrylates, simethicone, sodium alginate, sodium chloride, sorbitol, starch, pregelatinized starch, sucrose, sulfobutylether-cyclodextrin, talc, tragacanth, trehalose, and xylitol.

Diluents may be used in amounts calculated to obtain a desired volume for a tablet or capsule; in certain embodiments, a diluent is used in an amount of about 5% or more, about 10% or more, about 15% or more, about 20% or more, about 22% or more, about 24% or more, about 26% or more, about 28% or more, about 30% or more, about 32% or more, about 34% or more, about 36% or more, about 38% or more, about 40% or more, about 42% or more, about 44% or more, about 46% or more, about 48% or more, about 50% or more, about 52% or more, about 54% or more, about 56% or more, about 58% or more, about 60% or more, about 62% or more, about 64% or more, about 68% or more, about 70% or more, about 72% or more, about 74% or more, about 76% or more, about 78% or more, about 80% or more, about 85% or more, about 90% or more, or about 95% or more, weight/weight, of a drug core; between about 10% and about 90% w/w of the drug core; between about 20% and about 80% w/w of the drug core; between about 30% and about 70% w/w of the drug core; between about 40% and about 60% w/w of the drug core. In certain embodiments, a suitable amount of a particular diluent is determined by one of ordinary skill in the art.

In certain embodiments, formulations provided herein comprise one or more lubricants. Lubricants may be used, e.g., to facilitate tablet manufacture; examples of suitable lubricants include, for example, vegetable oils such as peanut oil, cottonseed oil, sesame oil, olive oil, corn oil, and oil of theobroma, glycerin, magnesium stearate, calcium stearate, and stearic acid. In certain embodiments, stearates, if present, represent no more than approximately 2 weight % of the drug-containing core. Further examples of lubricants include, e.g., calcium stearate, glycerin monostearate, glyceryl behenate, glyceryl palmitostearate, magnesium lauryl sulfate, magnesium stearate, myristic acid, palmitic acid, poloxamer, polyethylene glycol, potassium benzoate, sodium benzoate, sodium chloride, sodium lauryl sulfate, sodium stearyl fumarate, stearic acid, talc, and zinc stearate. In particular embodiments, the lubricant is magnesium stearate.

In certain embodiments, the lubricant is present, relative to the drug core, in an amount of about 0.2% w/w of the drug core, about 0.4% w/w of the drug core, about 0.6% w/w of the drug core, about 0.8% w/w of the drug core, about 1.0% w/w of the drug core, about 1.2% w/w of the drug core, about 1.4% w/w of the drug core, about 1.6% w/w of the drug core, about 1.8% w/w of the drug core, about 2.0% w/w of the drug core, about 2.2% w/w of the drug core, about 2.4% w/w of the drug core, about 2.6% w/w of the drug core, about 2.8% w/w of the drug core, about 3.0% w/w of the drug core, about 3.5% w/w of the drug core, about 4% w/w of the drug core, about 4.5% w/w of the drug core, about 5% w/w of the drug core, about 6% w/w of the drug core, about 7% w/w of the drug core, about 8% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 25% w/w of the drug core, about 30% w/w of the drug core, about 35% w/w of the drug core, about 40% w/w of the drug core, between about 0.2% and about 10% w/w of the drug core, between about 0.5% and about 5% w/w of the drug core, or between about 1% and about 3% w/w of the drug core. In certain embodiments, a suitable amount of a particular lubricant is determined by one of ordinary skill in the art.

In certain embodiments, formulations provided herein comprise one or more disintegrants. Disintegrants may be used, e.g., to facilitate disintegration of the tablet, and may be, e.g., starches, clays, celluloses, algins, gums or cross-linked polymers. Disintegrants also include, e.g., alginic acid, carboxymethylcellulose calcium, carboxymethylcellulose sodium (e.g., AC-DI-SOL, PRIMELLOSE), colloidal silicon dioxide, croscarmellose sodium, crospovidone (e.g., KOLLIDON, POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB) and starch. Additional disintegrants include, e.g., calcium alginate, chitosan, sodium docusate, hydroxypropyl cellulose, and povidone.

In certain embodiments, the disintegrant is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, greater than about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular disintegrant is determined by one of ordinary skill in the art.

In certain embodiments, formulations provided herein comprise one or more stabilizers. Stabilizers (also called absorption enhancers) may be used, e.g., to inhibit or retard drug decomposition reactions that include, by way of example, oxidative reactions. Stabilizing agents include, e.g., d-Alpha-tocopheryl polyethylene glycol 1000 succinate (Vitamin E TPGS), acacia, albumin, alginic acid, aluminum stearate, ammonium alginate, ascorbic acid, ascorbyl palmitate, bentonite, butylated hydroxytoluene, calcium alginate, calcium stearate, calcium carboxymethylcellulose, carrageenan, ceratonia, colloidal silicon dioxide, cyclodextrins, diethanolamine, edetates, ethylcellulose, ethyleneglycol, palmitostearate, glycerin monostearate, guar gum, hydroxypropyl cellulose, hypromellose, invert sugar, lecithin, magnesium aluminum silicate, monoethanolamine, pectin, poloxamer, polyvinyl alcohol, potassium alginate, potassium polacrilin, povidone, propyl gallate, propylene glycol, propylene glycol alginate, raffinose, sodium acetate, sodium alginate, sodium borate, sodium carboxymethyl cellulose, sodium stearyl fumarate, sorbitol, stearyl alcohol, sufobutyl-b-cyclodextrin, trehalose, white wax, xanthan gum, xylitol, yellow wax, and zinc acetate.

In certain embodiments, the stabilizer is, relative to the drug core, present in the amount of about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular stabilizer is determined by one of ordinary skill in the art.

In certain embodiments, formulations provided herein comprise one or more glidants. Glidants may be used, e.g., to improve the flow properties of a powder composition or granulate or to improve the accuracy of dosing. Excipients that may function as glidants include, e.g., colloidal silicon dioxide, magnesium trisilicate, powdered cellulose, starch, tribasic calcium phosphate, calcium silicate, powdered cellulose, colloidal silicon dioxide, magnesium silicate, magnesium trisilicate, silicon dioxide, starch, tribasic calcium phosphate, and talc.

In certain embodiments, the glidant is, relative to the drug core, present in the amount of less than about 1% w/w of the drug core, about 1% w/w of the drug core, about 2% w/w of the drug core, about 3% w/w of the drug core, about 4% w/w of the drug core, about 5% w/w of the drug core, about 6% w/w of the drug core, about 7% w/w of the drug core, about 8% w/w of the drug core, about 9% w/w of the drug core, about 10% w/w of the drug core, about 12% w/w of the drug core, about 14% w/w of the drug core, about 16% w/w of the drug core, about 18% w/w of the drug core, about 20% w/w of the drug core, about 22% w/w of the drug core, about 24% w/w of the drug core, about 26% w/w of the drug core, about 28% w/w of the drug core, about 30% w/w of the drug core, about 32% w/w of the drug core, between about 1% and about 10% w/w of the drug core, between about 2% and about 8% w/w of the drug core, between about 3% and about 7% w/w of the drug core, or between about 4% and about 6% w/w of the drug core. In certain embodiments, a suitable amount of a particular glidant is determined by one of ordinary skill in the art.

In certain embodiments, formulations provided herein comprise one or more permeation enhancers (also called, e.g., permeability enhancers). In certain embodiments, the permeation enhancer enhances the uptake of MIV-818 through the gastrointestinal wall. In certain embodiments, the permeation enhancer alters the rate and/or amount of MIV-818 that enters the bloodstream. In particular embodiments, d-alpha-tocopheryl polyethylene glycol-1000 succinate (Vitamin E TPGS) is used as a permeation enhancer. In particular embodiments, one or more other suitable permeation enhancers are used, including, e.g., any permeation enhancer known in the art. Specific examples of suitable permeation enhancers include, e.g., those listed below:

Example of Product Name Chemical Name Supplier

Pluronic F 127 Poloxamer F 127 Sigma
Lutrol F 68 Poloxamer 188 BASF
Carbopol 934-P Carbomer 934-P Spectrum Chemical
Tween 80 Polysorbate 80 Sigma
Chitosan Chitosan Low Mol Wt Aldrich
Capric acid/Na cap Sodium Decanoate Sigma
Lauric acid/Na laur Sodium Dodecanoate Sigma
Disodium EDTA Ethylenediamine tetraacetic acid Sigma disodium dehydrate
Propylene glycol 1, 2 Propanediol Sigma
CM Cellulose Carboxymethyl Cellulose Sigma
Labrasol Caprylocaproyl macrogol-8 glycerides Gattefosse
N,N-Dimethylacetamide (minimum 99%) Sigma
Vitamin E TPGS d-Alpha-Tocopheryl Polyethylene Eastman Glycol-1000 Succinate
Solutol HS 15 Polyethylene glycol 660 12-BASF hydroxystearate
Labrafil M 1944 CS (2) Oleyl Macrogolglyerides Gattefosse Other potential permeation enhancers include, e.g., alcohols, dimethyl sulfoxide, glyceryl monooleate, glycofurol, isopropyl myristate, isopropyl palmitate, lanolin, linoleic acid, myristic acid, oleic acid, oleyl alcohol, palmitic acid, polyoxyethylene alkyl ethers, 2-pyrrolidone, sodium lauryl sulfate, and thymol.

In certain embodiments, the permeation enhancer is present in the formulation in an amount by weight, relative to the total weight of the formulation, of about 0.1%, about 0.2%, about 0.3%, about 0.4%, about 0.5%, about 0.6%, about 0.7%, about 0.8%, about 0.9%, about 1%, about 1.1%, about 1.2%, about 1.3%, about 1.4%, about 1.5%, about 1.6%, about 1.7%, about 1.8%, about 1.9%, about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9%, about 4%, about 4.1% about 4.2%, about 4.3%, about 4.4%, about 4.5%, about 4.6%, about 4.7%, about 4.8%, about 4.9%, about 5%, about 5.1% about 5.2%, about 5.3%, about 5.4%, about 5.5%, about 5.6%, about 5.7%, about 5.8%, about 5.9%, about 6%, about 6.1% about 6.2%, about 6.3%, about 6.4%, about 6.5%, about 6.6%, about 6.7%, about 6.8%, about 6.9%, about 7%, about 7.1% about 7.2%, about 7.3%, about 7.4%, about 7.5%, about 7.6%, about 7.7%, about 7.8%, about 7.9%, about 8%, about 8.1% about 8.2%, about 8.3%, about 8.4%, about 8.5%, about 8.6%, about 8.7%, about 8.8%, about 8.9%, about 9%, about 9.1% about 9.2%, about 9.3%, about 9.4%, about 9.5%, about 9.6%, about 9.7%, about 9.8%, about 9.9%, about 10%, greater than about 10%, greater than about 12%, greater than about 14%, greater than about 16%, greater than about 18%, greater than about 20%, greater than about 25%, greater than about 30%, greater than about 35%, greater than about 40%, greater than about 45%, or greater than about 50%. In certain embodiments, the appropriate amount of a suitable permeation enhancer provided herein is determined by one of skill in the art.

Without intending to be limited to any particular theory, the permeation enhancers provided herein may function by, inter alia, facilitating (e.g., increasing the rate or extent of) the transport of MIV-818 through the gastrointestinal wall. In general, movement through the gastrointestinal wall may occur by, e.g.: passive diffusion, such as the movement of drug across a membrane in a manner driven solely by the concentration gradient; carrier-mediated diffusion, such as the movement of drug across a cell membrane via a specialized transport system embedded in the cell membrane; paracellular diffusion, such as the movement of a drug across a membrane by going between, rather than through, two cells; and transcellular diffusion, such as the movement of a drug across the cell.

Additionally, there are numerous cellular proteins capable of preventing intracellular accumulation of drugs by pumping out drug that enters the cell. These are sometimes called efflux pumps. One such efflux pump is that involving p-glycoprotein, which is present in many different tissues in the body (e.g., intestine, placental membrane, blood-brain barrier). Permeation enhancers can function by, inter alia, facilitating any of the processes mentioned above (such as by increasing fluidity of membranes, opening tight junctions between cells, and/or inhibiting efflux, among others).

In one embodiment, the anti-PD1/anti-PDL1 monoclonal antibody is administered on days 7 and 21 in a 28-day cycle.

In one embodiment, the anti-PD1/anti-PDL1 monoclonal antibody is administered on day 1 in a 28-day cycle.

In one embodiment, the anti-PD1/anti-PDL1 monoclonal antibody is administered on days 8 and 21 in a 28-day cycle.

In one embodiment, the anti-PD1/anti-PDL1 monoclonal antibody is administered on day 1 in a 21-day cycle.

In one embodiment, the anti-PD1/anti-PDL1 monoclonal antibody is administered on day 1 in a 14-day cycle.

In one embodiment the MIV-818 is administered in an amount of about 50 mg, about 100 mg, about 200 mg, about 300 mg, about 400 mg, about 500 mg, or about 600 mg per day.

In one embodiment, the MIV-818 is administered in an amount of about 300 mg per day.

In one embodiment, the MIV-818 is administered in an amount of about 200 mg per day.

In one embodiment, the MIV-818 is administered once per day.

In one embodiment, the MIV-818 is administered twice per day.

In one embodiment, the MIV-818 is administered in an amount of about 200 mg, about 150 mg, or about 100 mg twice per day. In one embodiment, the MIV-818 is administered in an amount of about 200 mg, twice per day. In one embodiment, the MIV-818 is administered in an amount of about 150 mg twice per day. In one embodiment, the MIV-818 is administered in an amount of about 100 mg twice per day.

In one embodiment, the anti-PD1/anti-PDL1 monoclonal antibody is administered parenterally.

In one embodiment, the anti-PD1/anti-PDL1 monoclonal antibody is administered in an amount of about 0.5 mg of anti-PD1/anti-PDL1 monoclonal antibody per kilogram of a subject's mass, about 1 mg/Kg, about 2 mg/Kg, about 3 mg/Kg, about 4 mg/Kg, about 5 mg/Kg, about 6 mg/Kg, about 7 mg/Kg, about 8 mg/Kg, about 9 mg/Kg, about 10 mg/Kg, about 11 mg/Kg, about 12 mg/Kg, about 13 mg/Kg, about 14 mg/Kg, about 15 mg/Kg, about 16 mg/Kg, about 17 mg/Kg, about 18 mg/Kg, about 19 mg/Kg, or about 20 mg/Kg.

In one embodiment, the anti-PD1/anti-PDL1 monoclonal antibody is administered intravenously in an amount of about 10 mg/Kg per day.

In one embodiment, the anti-PD1/anti-PDL1 monoclonal antibody is administered intravenously in an amount of about 10 mg/Kg per day on days 7 and 21 in a 28-day cycle, or on days 8 and 21 in a 28-day cycle.

In one embodiment, the anti-PD1 monoclonal antibody is pembrolizumab, MK-3475, pidilizumab, Nivolumab (BMS-936558, MDX-1106, or ONO-4538) and is administered as a 30 minute i.v.infusion.

In one embodiment, the anti-PDL1 monoclonal antibody is BMS-936559, atezolizumab (MPDL3280A), or durvalumab (MEDI4736) and is administered as a 30 minute i.v.infusion.

In one embodiment, 1,500 mg of durvalumab (MEDI4736) is administered on Day 1 of each 28-day treatment cycle by 1-hour intravenous (IV) infusion.

In certain embodiments, the method of treating liver tumours comprises orally administering a formulation comprising the MIV-818 as single or multiple daily doses.

In particular embodiments, the formulation(s) comprising the MIV-818 is/are orally administered once per day, twice per day, three times per day, four times per day, or more than four times per day. For example, in certain embodiments, the formulation comprising the MIV-818 is administered using a treatment cycle comprising administration of about 200 mg, about 300 mg, about 400 mg, about 500 mg, about 600 mg, about 700 mg, about 800 mg, about 900 mg, or about 1,000 mg of the once, twice, three, or four times per day for 7, 8, 9, 10, 11, 12, 13, 14, 15, 16, 17, 18, 19, 20, 21, 22, 23, 24, 25, 26, 27, 28, 29, or 30 days.

In certain embodiments, the method of treating comprises continuous low-dose administration. In certain embodiments, the formulation comprising the MIV-818 is administered using a treatment cycle comprising administration of about 300 mg of the MIV-818 twice per day for 7 days. In certain embodiments, the formulation comprising the MIV-818 is administered using a treatment cycle comprising administration of about 300 mg of the MIV-818 twice per day for 14 days. In certain embodiments, the formulation comprising the MIV-818 is administered using a treatment cycle comprising administration of about 300 mg of the MIV-818 three times per day for 7 days. In certain embodiments, the formulation comprising the MIV-818 is administered using a treatment cycle comprising administration of about 300 mg of the MIV-818 three times per day for 14 days.

In certain embodiments, methods provided herein comprise administering a formulation comprising MIV-818 using one or more of the cycles provided herein, and repeating one or more of the cycles for a period of, e.g., 1, 2, 3, 4, 5, 6, 7, 8, 9, 10, 11, 12, or greater than 12 months.

In certain embodiments, methods provided herein comprise administering daily to a subject an oral formulation of the MIV-818 for 7 or more, 8 or more, 9 or more, 10 or more, 11 or more, 12 or more, 13 or more, 14 or more, 15 or more, 16 or more, 17 or more, 18 or more, 19 or more, 20 or more, or 21 or more days.

In certain embodiments, the dosage of the MIV-818 may range, e.g., between about 50 mg/m$^2$/day and about 2,000 mg/m$^2$/day, between about 100 mg/m$^2$/day and about 1,000 mg/m$^2$/day, between about 100 mg/m$^2$/day and about 500 mg/m$^2$/day, or between about 120 mg/m$^2$/day and about 250 mg/m$^2$/day. In certain embodiments, particular dosages are, e.g., about 120 mg/m$^2$/day, about 140 mg/m$^2$/day, about 150 mg/m$^2$/day, about 180 mg/m$^2$/day, about 200 mg/m$^2$/day, about 220 mg/m$^2$/day, about 240 mg/m$^2$/day, about 250 mg/m$^2$/day, about 260 mg/m$^2$/day, about 280 mg/m$^2$/day, about 300 mg/m$^2$/day, about 320 mg/m$^2$/day, about 350 mg/m$^2$/day, about 380 mg/m$^2$/day, about 400 mg/m$^2$/day, about 450 mg/m$^2$/day, or about 500 mg/m$^2$/day.

VI. EXAMPLES

Example 1

In Vitro Model of Tumour Immune Microenvironment Assay

As described above, MIV-818 is extremely unstable in rodent plasma and therefore cannot be used in standard murine models reflecting the role of the immune system in oncogenesis and cancer treatment. We have therefore employed the complex cell culture model of the tumour immune microenvironment, BioMAP commercially provided by Eurofins Scientific subsidiary DiscoverX (www.discoverx.com). This system has the further advantage that it uses human cells, thereby allowing the use of human PDL-1 monoclonals (such as pembrolizumab) which are not active in the mouse, in comparison to murine models which require the PDL-1 monoclonal to be replaced with a murine equivalent.

To recapitulate the complex signaling networks that manifest in the multi-component TME, the BioMAP Oncology systems co-culture human primary immune cells with primary tissue cells in the presence of a specific cancer cell line. These co-cultures are stimulated with submitogenic levels of T cell receptor (TCR) ligands to prime, but not maximally activate T cells and model immune cells recruited to the intra-tumoural microenvironment.

There are two BioMAP Oncology panels that model the interactions between the immune-stromal (fibroblasts) and immune-vascular (endothelial cells) environments in the context of colon cancer (HT-29 CRC cell line), or in the context of non-small lung cancer (NCI-H1299 NSCLC cell line). The interactions between tumour cells, stimulated immune cells (peripheral blood mononuclear cells (PBMC)), and the host stromal network (human neonatal dermal fibroblasts (HDFn)) is captured in the Stro Oncology systems. In parallel, the Vasc systems capture the interactions between tumour cells, activated immune cells and the vascular tissue (human umbilical vein endothelial cells (HUVEC). The biomarkers selected for the Oncology panels inform on activities related to inflammation, immune-function, tissue remodeling and metastasis in the context of a host tumour-microenvironment. Collectively, the Oncology CRC panel and the Oncology NSCLC panel.

Human primary cells in BioMAP systems are used at early passage (passage 4 or earlier) to minimize adaptation to cell culture conditions and preserve physiological signaling responses. All primary cells are pooled from multiple donors (n=3-6), commercially purchased and handled according to the recommendations of the manufacturers. The HT-29 CRC cell line and the NCI-H1299 NSCLC cell line are purchased from American Type Culture Collection (ATCC). Abbreviations are used as follows: human umbilical vein endothelial cells (HUVEC), peripheral blood mononuclear cells (PBMC), human neonatal dermal fibroblasts (HDFn) and T cell receptor (TCR). Systems in both the Oncology CRC and NSCLC panels are stimulated by submitogenic levels of super antigens (SAg) acting via the TCR to recapitulate the recruitment of immune cells to the tumour environment in situ. These stimulation conditions are optimized to activate or prime T cells, but not drive T cell proliferation.

Cell types used in each of the CRC systems are as follows: StroHT29 system [HT-29 colorectal adenocarcinoma cell line+HDFn+PBMC] and VascHT29 system [HT-29 colorectal adenocarcinoma cell line+HUVEC+PBMC]. Without wishing to be bound by theory it is believed that the StroHT29 system is particularly well suited to modelling HCC, given the importance of stromal tissue in HCC, and the observation that HT-29 are also sensitive to MIV-818 alone (around 0.02 uM) with a comparable $IC_{50}$ to representative HCC cell lines (eg HepG2 around 0.02 uM).

All primary human cells were obtained under protocols that were reviewed by Institutional Review Board(s) (IRB) that operate in accordance with the requirement of the EPA Regulation 40 CFR 26 and HHS Regulation 45 CFR 46 of the US Department of Health and Human Resources for the protection of human research subjects.

In the accompanying Figures, the biomarkers left to right are:

| StroHT29 | VascHT29 |
|---|---|
| CD106/VCAM-1 | CCL2/MCP-1 |
| CD87/uPAR | CD106/VCAM-1 |
| CEACAM5/CD66e | CD40 |
| Collagen I | CD69 |
| Collagen III | CD87/uPAR |
| CXCL10/P-10 | CEACAM5/CD66e |
| Keratin 20 | Collagen IV |
| MMP-9 | CXCL10/P-10 |
| PAI-I | CXCL9/MIG |
| PBMC cytotoxicity | Keratin 20 |
| sGranzyme B | PBMC cytotoxicity |
| sIFNg | sGranzyme B |
| sIL-10 | sIFNg |
| sIL-17A | sIL-10 |
| sIL-2 | sIL-17A |
| sIL-6 | sIL-2 |
| SRB | sIL-6 |
| sTNF-alpha | SRB |
| sVEGF | sTNF-alpha |
| TMP-2 | |
| tPA | |
| uPA | |

In each of the BioMAP readouts in FIGS. 1-7, the Y axis is Log Ratio extending from −1.0 to +1.0. MIV-818 is coded MV087313.

Adherent cell types are cultured in 96-well plates until confluent, followed by the addition of PBMC. Test agents prepared in either DMSO (small molecules; final concentration ≤0.1%) or PBS (biologics) are added at the specified concentrations 1-hr before stimulation, and remain in culture for 48-hrs. Each plate contains drug controls (e.g., legacy control test agent colchicine), negative controls (e.g., non-stimulated condition) and vehicle controls (e.g., 0.1% DMSO). Direct ELISA is used to measure biomarker levels of cell-associated and cell membrane targets. Soluble factors from supernatants are quantified using either HTRF® detection, bead-based multiplex immunoassay or capture ELISA. Effects of test agents on cell viability (cytotoxicity) are measured by sulforhodamine B (SRB) for adherent cells (48-hrs), and by alamarBlue® reduction for cells in suspension (42-hrs) at the time points indicated. All test agents are tested in standardized formats at 4 concentrations, in triplicate. Colchicine stimulated wells, vehicle control treated wells, and wells without stimulation are included as controls on each plate (n=3-8). Data acceptance criteria are based on plate performance (% CV of controls), and the performance of positive controls across assays with a comparison to historical controls.

Data Analysis.

Biomarker measurements are profiled in triplicate for test agent-treated samples, and divided by the average of vehicle control samples (at least 6 vehicle controls from the same plate) to generate a ratio that is then log 10 transformed. Significance prediction envelopes are calculated using historical vehicle control data at a 95% confidence interval. Statistical p-values are calculated from unpaired t-test statistics of raw assay values compared to vehicle controls.

Profile Annotation—Biomarker activities are annotated when at least one concentration of the test agent is outside of the significance envelope with an effect size>20% compared to the vehicle control (|log 10 ratio|>0.1) and a p-value<0.01. Cytotoxic conditions occur when total protein levels decrease by more than 50% (log 10 ratio of SRB<−0.3) and are indicated by a thin black arrow above the X-axis. Concentrations of test agents with detectable broad cytotoxicity are excluded from biomarker activity annotation and downstream benchmark analysis. Cytotoxic arrows only require one concentration to meet the indicated log 10 ratio threshold for profile annotation and do not include a p-value requirement.

Overlay Analysis—The profile of one concentration of a test agent is compared to that of a nominated benchmark compound from the BioMAP Oncology panel benchmark list, or can be an overlay of another compound within the current client project or a previous project. Common biomarker readouts are annotated when the readout for both profiles is outside of the significance envelope with an effect size>20% (|log 10 ratio|>0.1) in the same direction. Differentiating biomarkers are annotated when one profile has a readout outside of the significance envelope with an effect size>20% (log 10 ratio|>0.1), and the readout for the other profile is either inside the envelope or in the opposite direction.

Analysis

Figure 1:
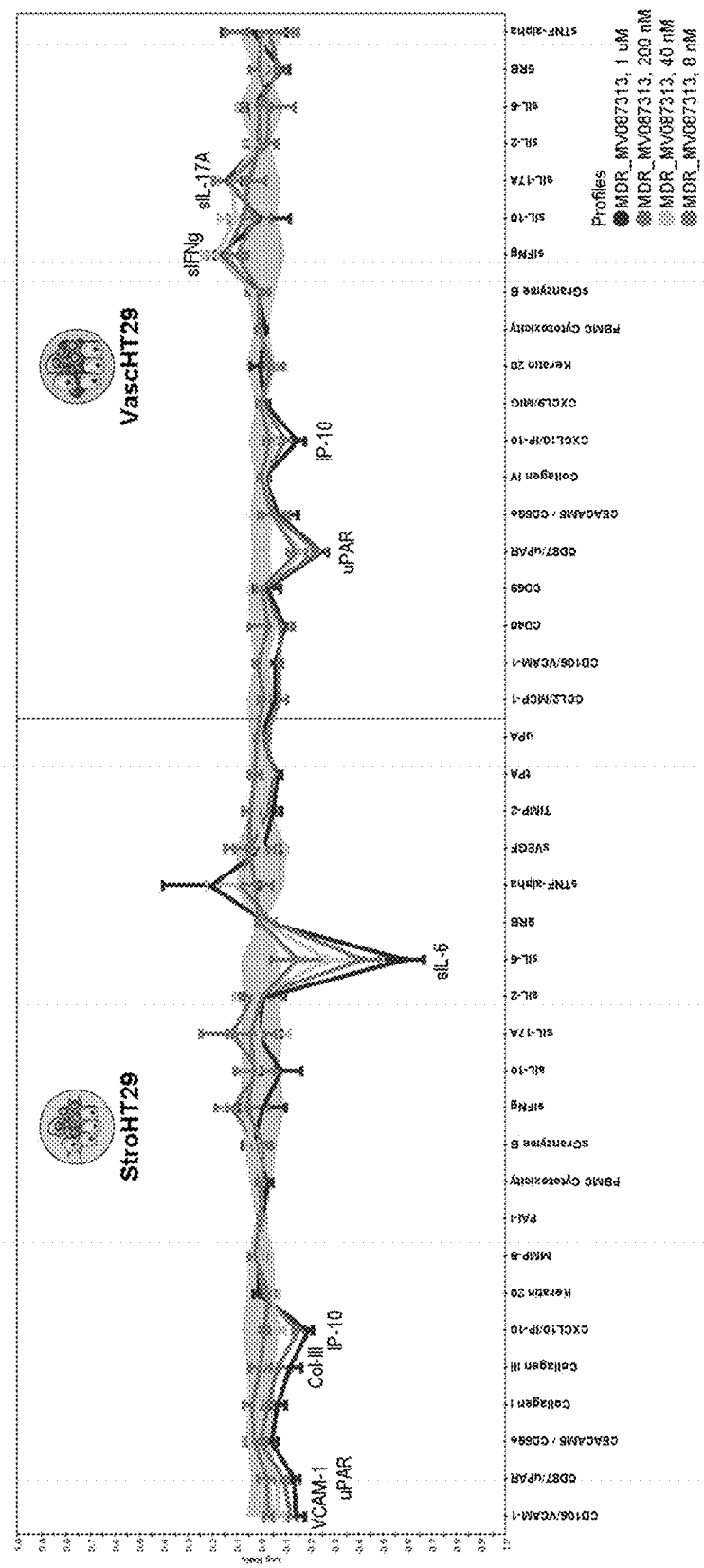
FIG. 1 is a BioMAP readout depicting the effect of MIV-818 in a complex cell culture model of the tumour immune microenvironment, as described further in Example 1.

Turning now to FIG. 1, it will be apparent that MIV-818 administered alone to the two panels, shows a distinctive pattern on the various immune markers, showing a good dose response on specific markers indicative of a stimulation of the immune system which may lead to an anti-tumour response. The doses of MIV-818 employed correspond to 1 uM, 200 nM, 40 nM and 8 nM. MIV-818 treatment of vascular or stromal models of HT-29 and peripheral blood mononuclear cells (PBMCs) leads to multiple changes in secreted proteins, indicating changes in different pathways:

Immune-related activities: decreased sIL-6; increased siL-17A, sIFNγ
Inflammation-related activities: decreased VCAM-1, IP-10
Matrix remodeling activities: decreased Collagen III
Angiogenesis-Related Activities: Decreased uPAR This finding is surprising and exciting, as MIV-818 was originally developed as a cytotoxic drug with direct activity on liver cells. This finding opens up for combining MIV-818 with a specific class of immune-oncologic agents, namely monoclonal antibodies which block the binding of PD-L1 and/or PD-L2 to PD-1, as shown in the following examples.

Figure 7:
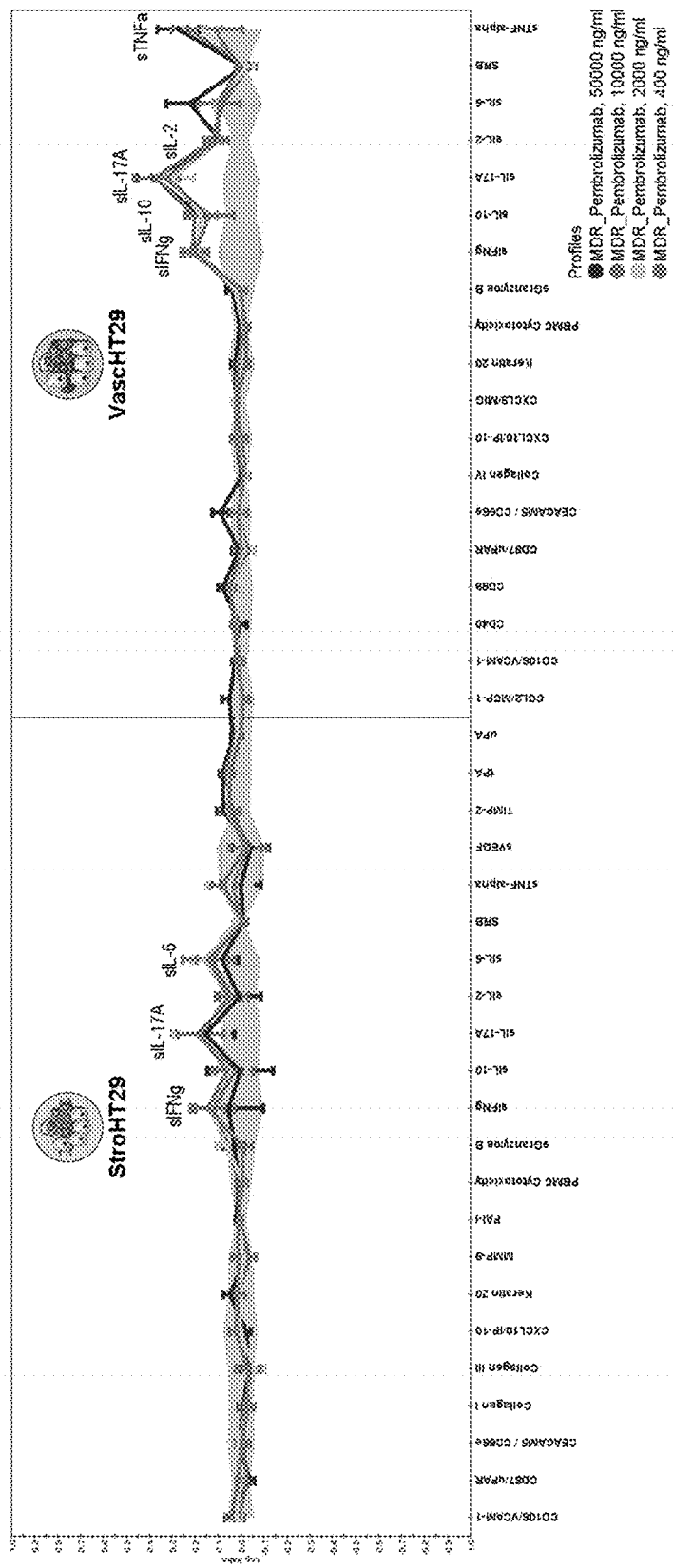
FIG. 7 is a BioMAP readout of the dose response of pembrolizumab, for comparison.

For comparison FIG. 7 depicts the corresponding assay of pembrolizumab alone on the two panels, at doses corresponding to 50 000 ng/ml, 10 000 ng/ml, 2 000 ng/ml and 400 ng/ml. Note in particular that the pattern of responses (positive, negative or no effect) and also the degree of dose-response with pembrolizumab differs markedly from FIG. 1.

Figure 2:
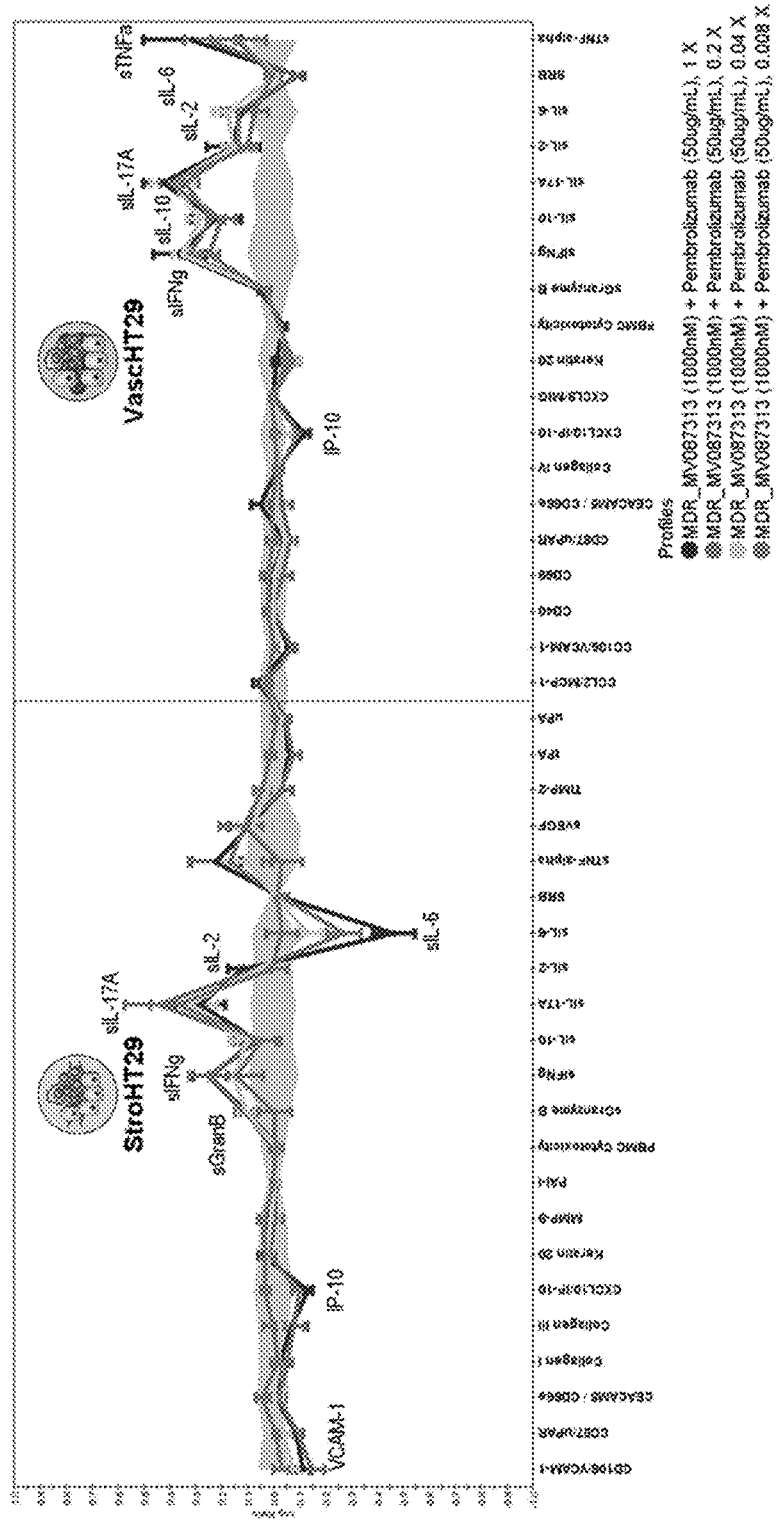
FIG. 2 is a BioMAP readout of the combination of 1000 nM MIV-818 and 50 ug/ml pembrolizumab.

FIG. 2 is a BioMAP readout of the combination envisaged by the invention—of a stock solution representing 1000 nM MIV-818 and 50 ug/ml pembrolizumab serially diluted
1×, (1000 nM MIV-818 and 50 ug/ml pembrolizumab)
0.2×, (200 nM MIV-818 and 10 ug/ml pembrolizumab)
0.04×, (40 nM MIV-818 and 2 ug/ml pembrolizumab)
0.008×, 8 nM MIV-818 and 0.4 ug/pembrolizumab)

The combination of MIV-818 and pembrolizumab leads to enhanced changes in a range of cytokines and secreted proteins, over and above the effects of the single agents.

Key activities of the combination include the following:
Increased immune-related activities: increased sIL-10, siL-17A, sGranB, siL-2, sIFNγ; modulated siL-6
Inflammation-related activities: decreased VCAM-1, IP-10; increased sTNFα

Figure 3:
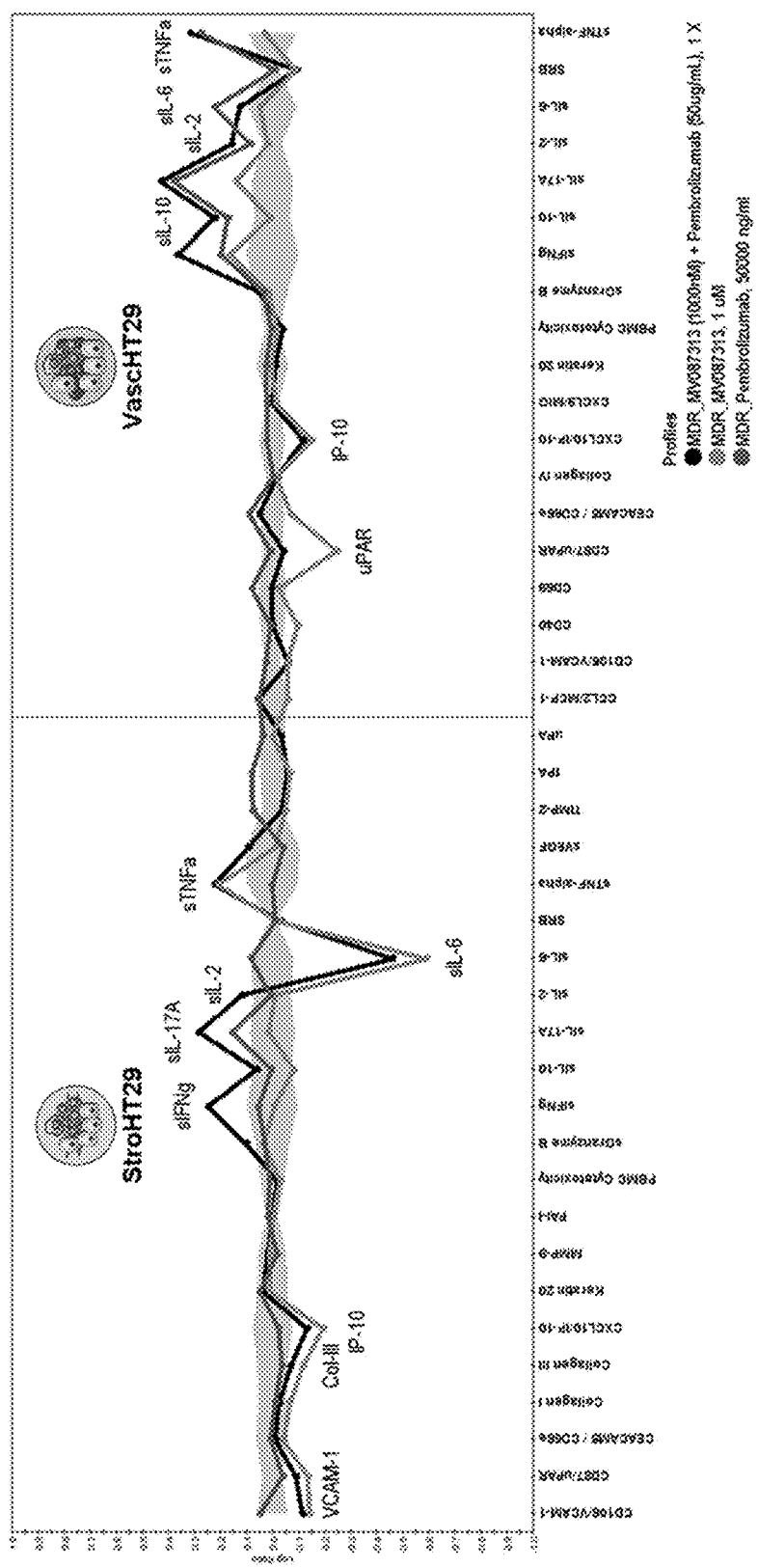
FIG. 3 is a BioMAP readout the 1000 nM MIV-818/50 ug pembrolizumab combination overlaid on the corresponding single agents.

FIG. 3 is a BioMAP readout of the combination 1000 nM MIV-818/50 ug pembrolizumab combination overlaid on the corresponding single agents. Note in particular that there are 14 differentiating activities that are annotated within the following systems: StroHT29 (VCAM-1, Collagen III, IP-10, sIFNγ, siL-17A, siL-2, sIL-6, sTNFα) and VascHT29 (uPAR, IP-10, sIL-10, siL-2, siL-6, sTNFα).

Figure 4:
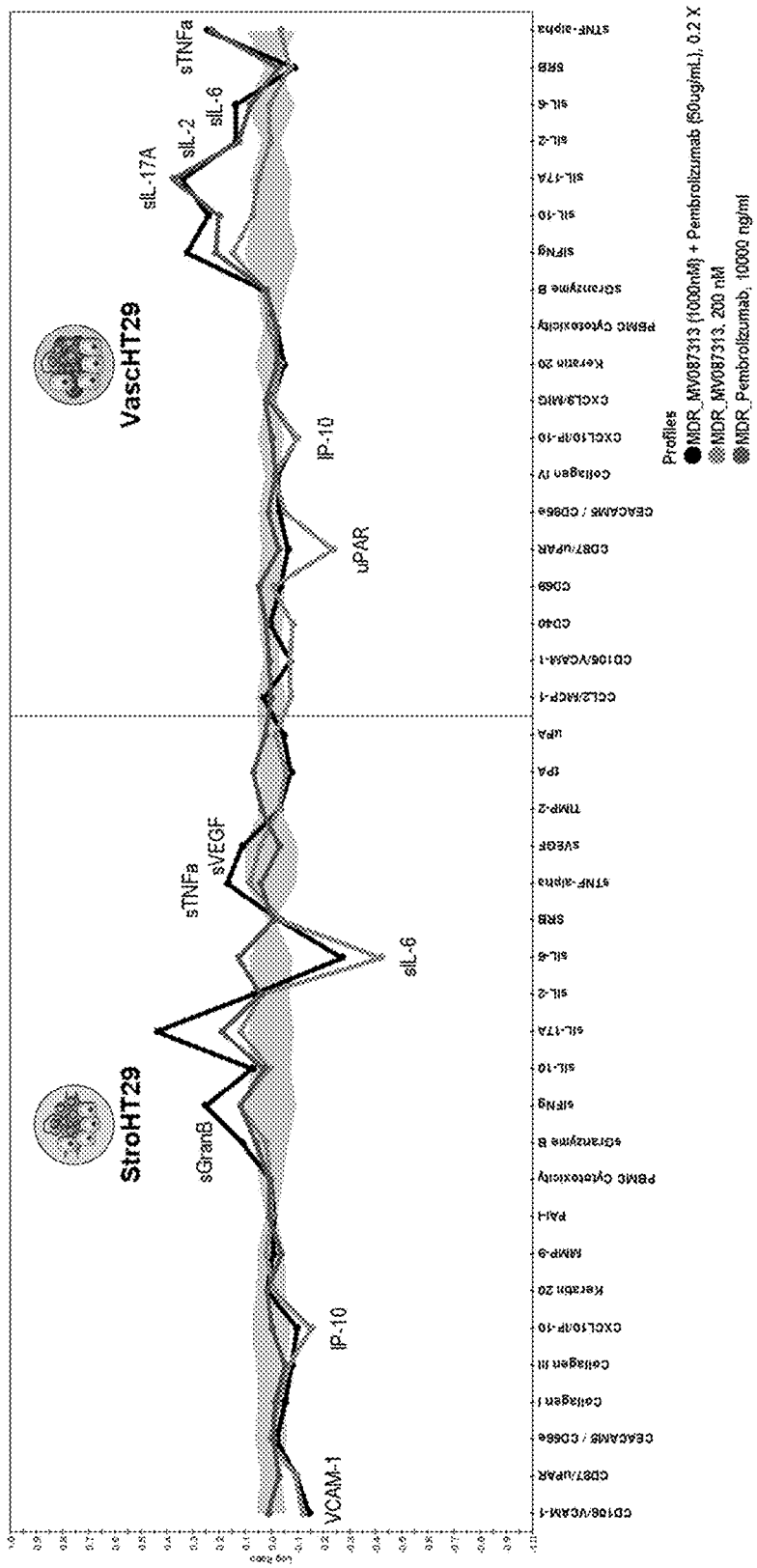
FIG. 4 is a BioMAP readout of the combination 200 nM MIV-818/10 ug/ml pembrolizumab, overlaid on the corresponding single agents.

FIG. 4 is a BioMAP readout of the combination 200 nM MIV-818/10 ug/ml pembrolizumab, overlaid on the corresponding single agents; There are 12 differentiating activities that are annotated within the following systems: StroHT29 (VCAM-1, IP-10, sGranB, siL-6, sTNFα, sVEGF) and VascHT29 (uPAR, IP-10, sIL-17A, siL-2, siL-6, sTNFα).

Figure 5:
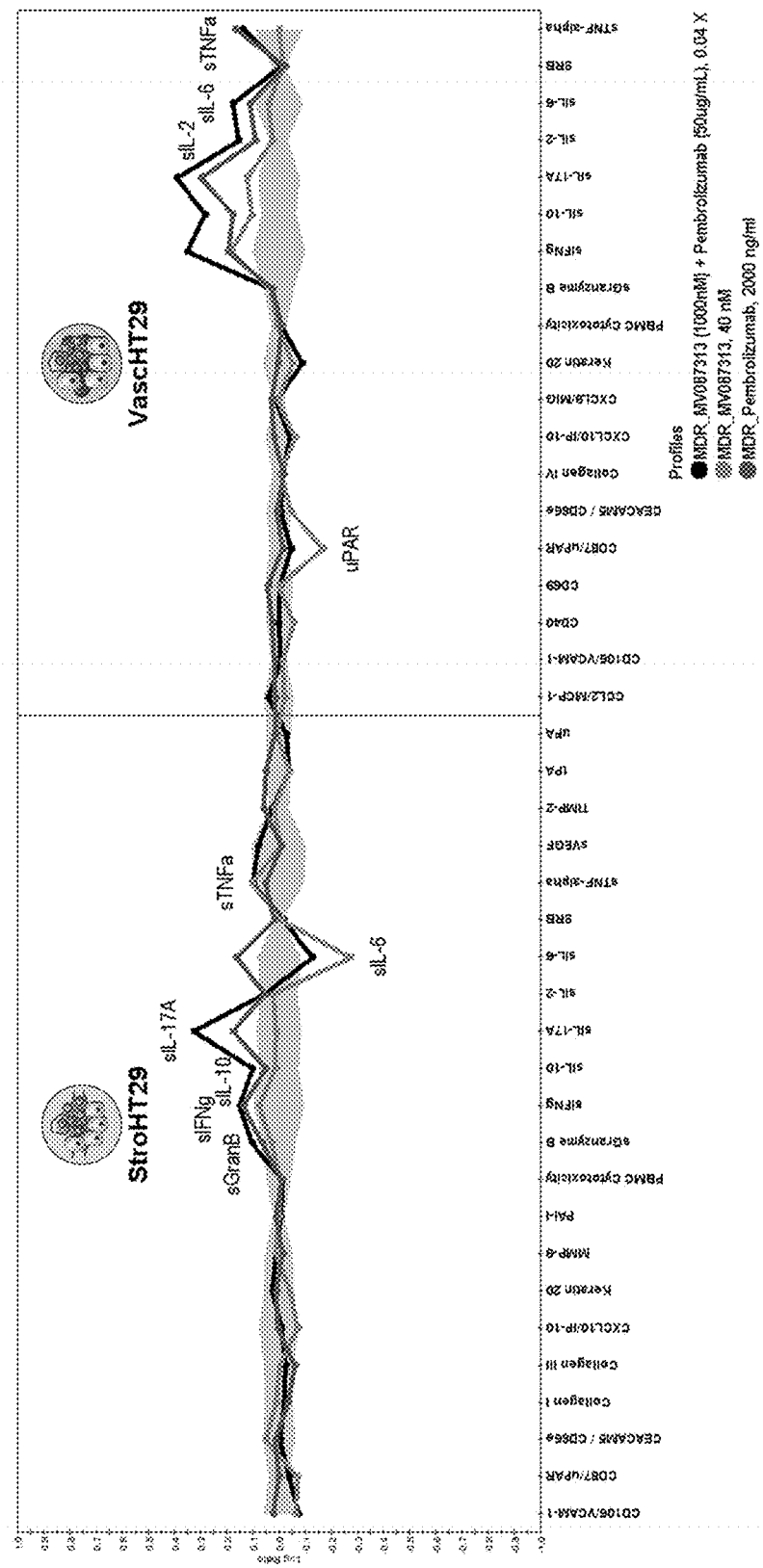
FIG. 5 is a BioMAP readout of the combination 40 nM MIV-818/2 ug/ml pembrolizumab, overlaid on the corresponding single agents.

FIG. 5 is a BioMAP readout of the combination 40 nM MIV-818/2 ug/ml pembrolizumab, overlaid on the corresponding single agents; There are 10 differentiating activities that are annotated within the following systems: StroHT29 (sGranB, sIFNγ, sIL-10, siL-17A, siL-6, sTNFα) and VascHT29 (uPAR, siL-2, siL-6, sTNFα).

Figure 6:
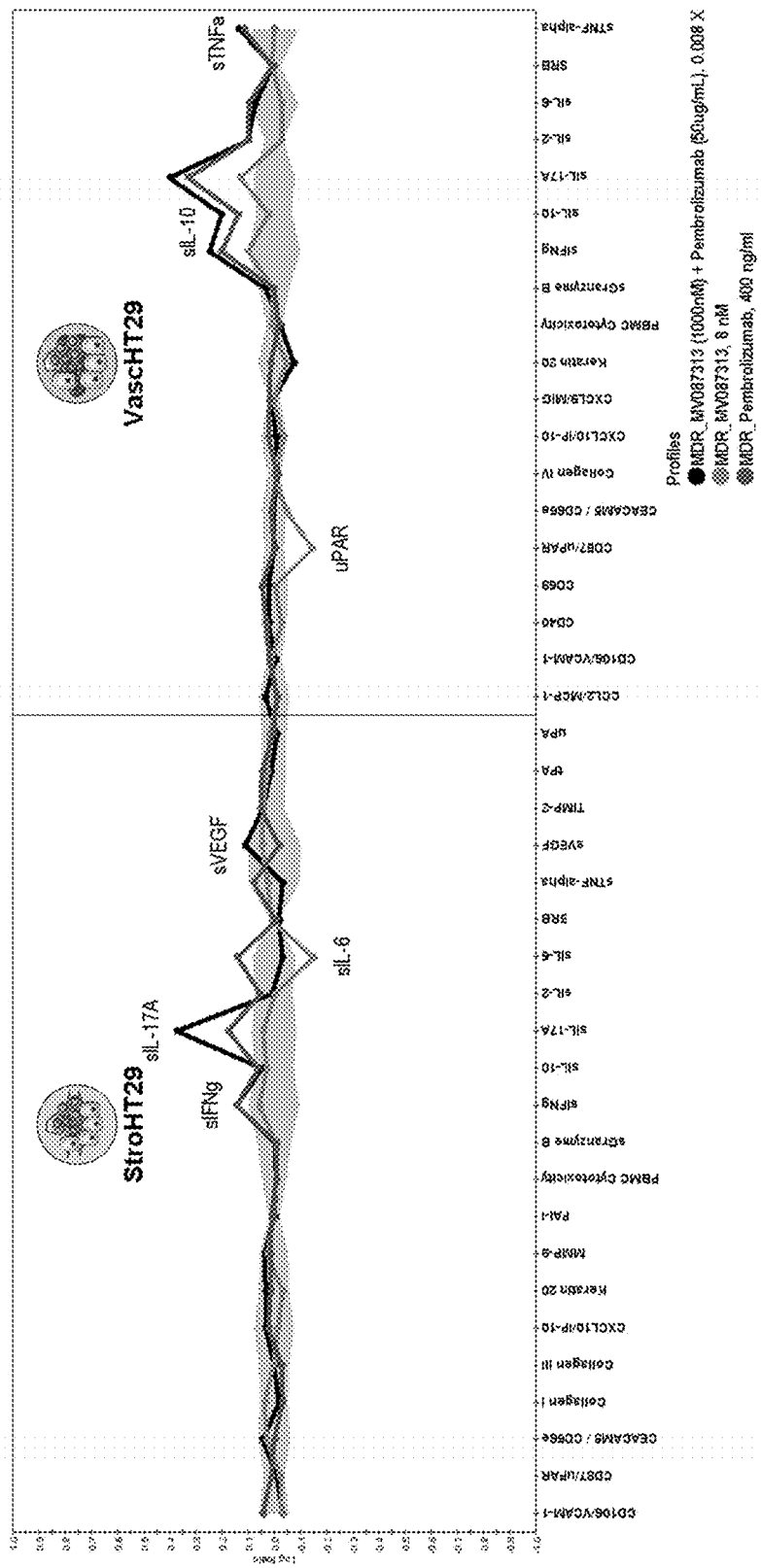
FIG. 6 is a BioMAP readout of the combination 8 nM MIV-818/0.4 ug/ml pembrolizumab, overlaid on the corresponding single agents.

FIG. 6 is a BioMAP readout of the combination 8 nM MIV-818/0.4 ug/ml pembrolizumab, overlaid on the corresponding single agents; There are 7 differentiating activities that are annotated within the following systems: StroHT29 (sIFNγ, siL-17A, siL-6, sVEGF) and VascHT29 (uPAR, sIL-10, sTNFα).

Figure 8:
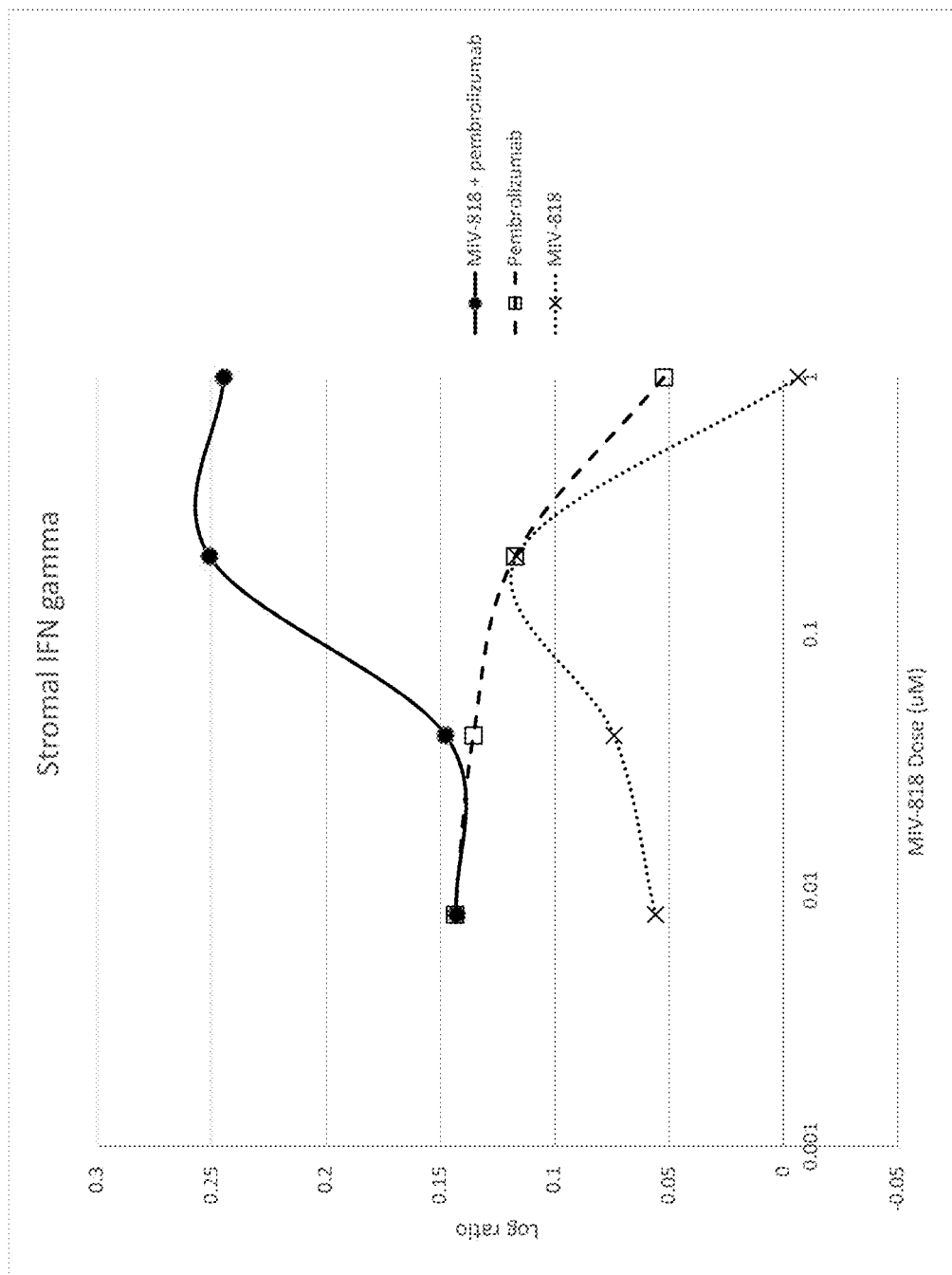
FIG. 8 is a plot showing the relationship between dose and effects of the components MIV-818 and pembrolizumab on stromal IFN gamma in the cell culture model of the tumour microenvironment.

FIGS. 2-6 can be better understood by plotting the individual distinctive markers. For example, MIV-818 enhances the immune-stimulating cytokine IFN-gamma in combination with pembolizumab, as depicted in FIG. 8 which is a plot showing the relationship between dose and ratio of the components MIV-818 and pembrolizumab on stromal IFN gamma in the cell culture model of the tumour microenvironment. Interferon Gamma (IFNγ) is a cytokine involved in the innate and adaptive immune response against infections. Soluble IFNγ (sIFNγ) exhibits context-dependent anti- and pro-tumourigenic activities, and is categorized as an immune-related activity in the StroHT29 system modeling the interaction between the immune-stromal (fibroblasts) environment in the context of a colon cancer cell line (CRC HT29).

Figure 9:
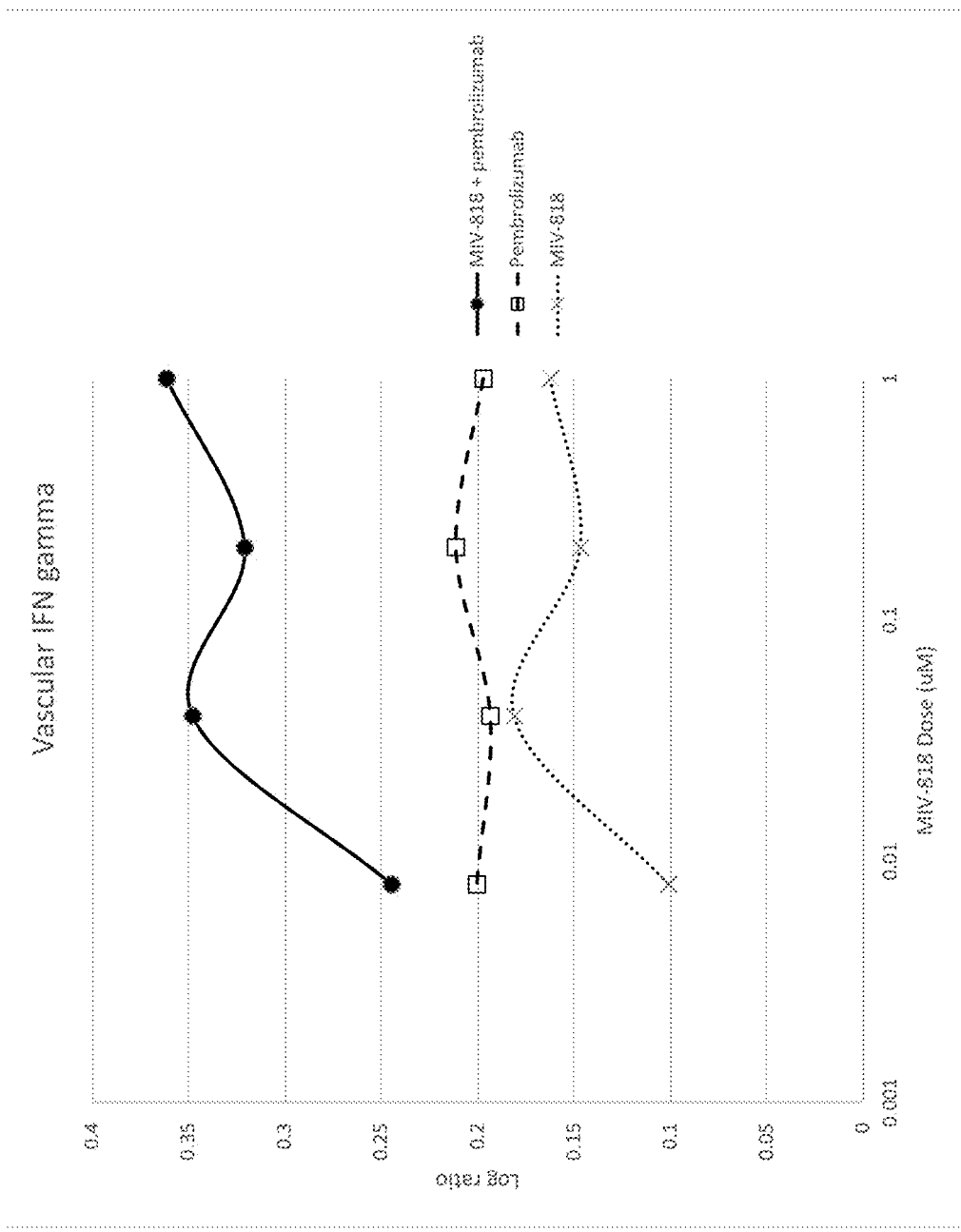
FIG. 9 is a plot showing the relationship between dose and effects of the components MIV-818 and pembrolizumab on vascular IFN gamma in the cell culture model of the tumour microenvironment.

The combination of MIV-818 and pembrolizumab shows a clear dose response enhanced sIFNγ in the stromal HT-29 system, compared to either agent alone, indicative of induction of an enhanced anti-tumour immune response. Similarly, FIG. 9 shows an enhanced anti-tumour immune response for vascular IFN gamma.

Figure 10:
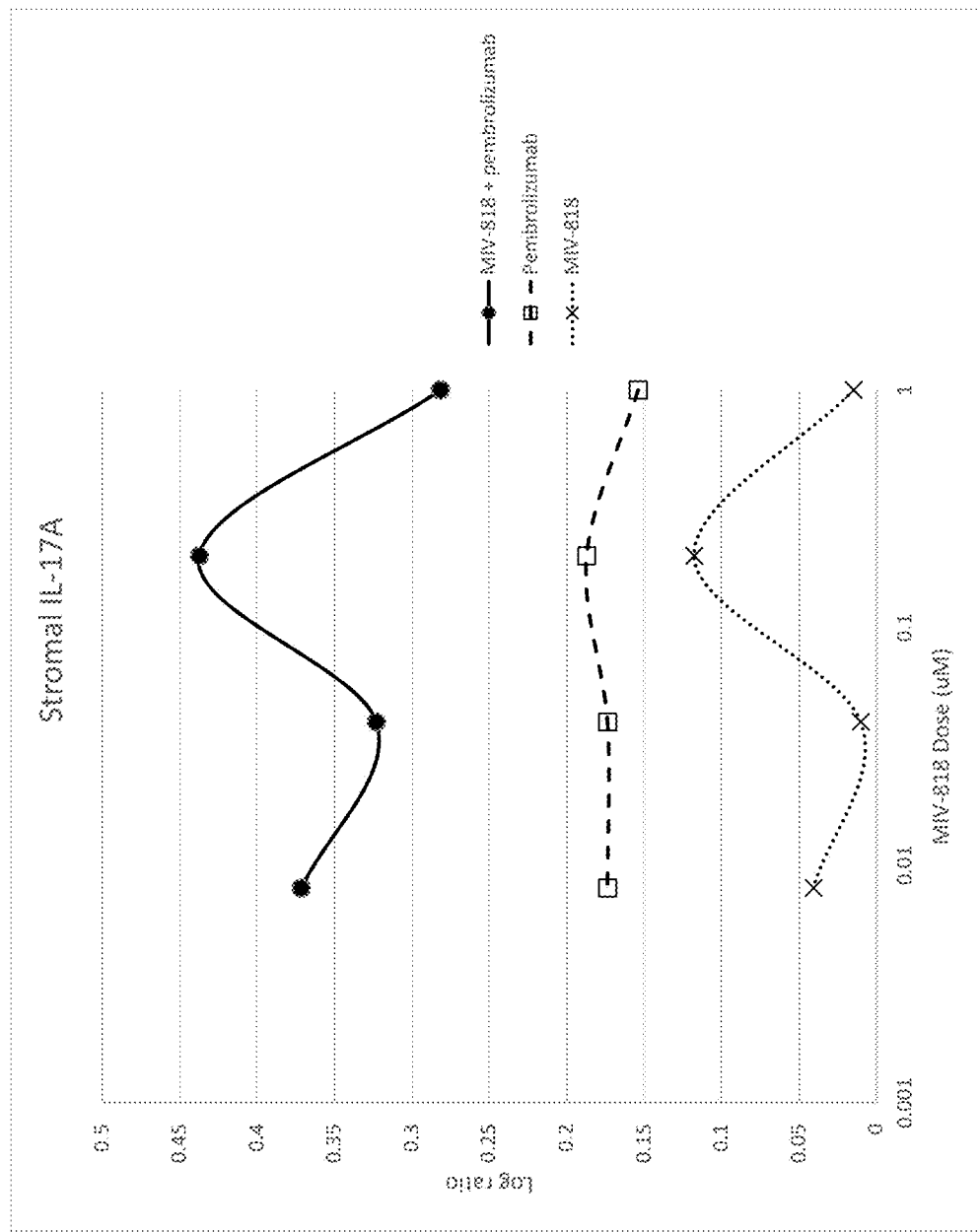
FIG. 10 is a plot showing the relationship between dose and effects of the components MIV-818 and pembrolizumab on stromal IL17A in the cell culture model of the tumour microenvironment.

FIG. 10 is a plot showing the relationship between dose and ratio of the components MIV-818 and pembrolizumab on stromal IL7A in the cell culture model of the tumour microenvironment; Interleukin 17A (IL-17A) is a pro-inflammatory cytokine secreted by a subset of activated T cells (Th17 cells), γδT cells and neutrophils. IL-17A exhibits both pro-tumour functions (angiogenesis and metastasis) and anti-tumour functions (induction of cytolytic T cell responses). Soluble IL-17A (siL-17A) is categorized as an immune-related activity in the StroHT29 system modeling the interaction between the immune-stromal (fibroblasts) environment in the context of a colon cancer cell line (CRC HT29).

Figure 11:
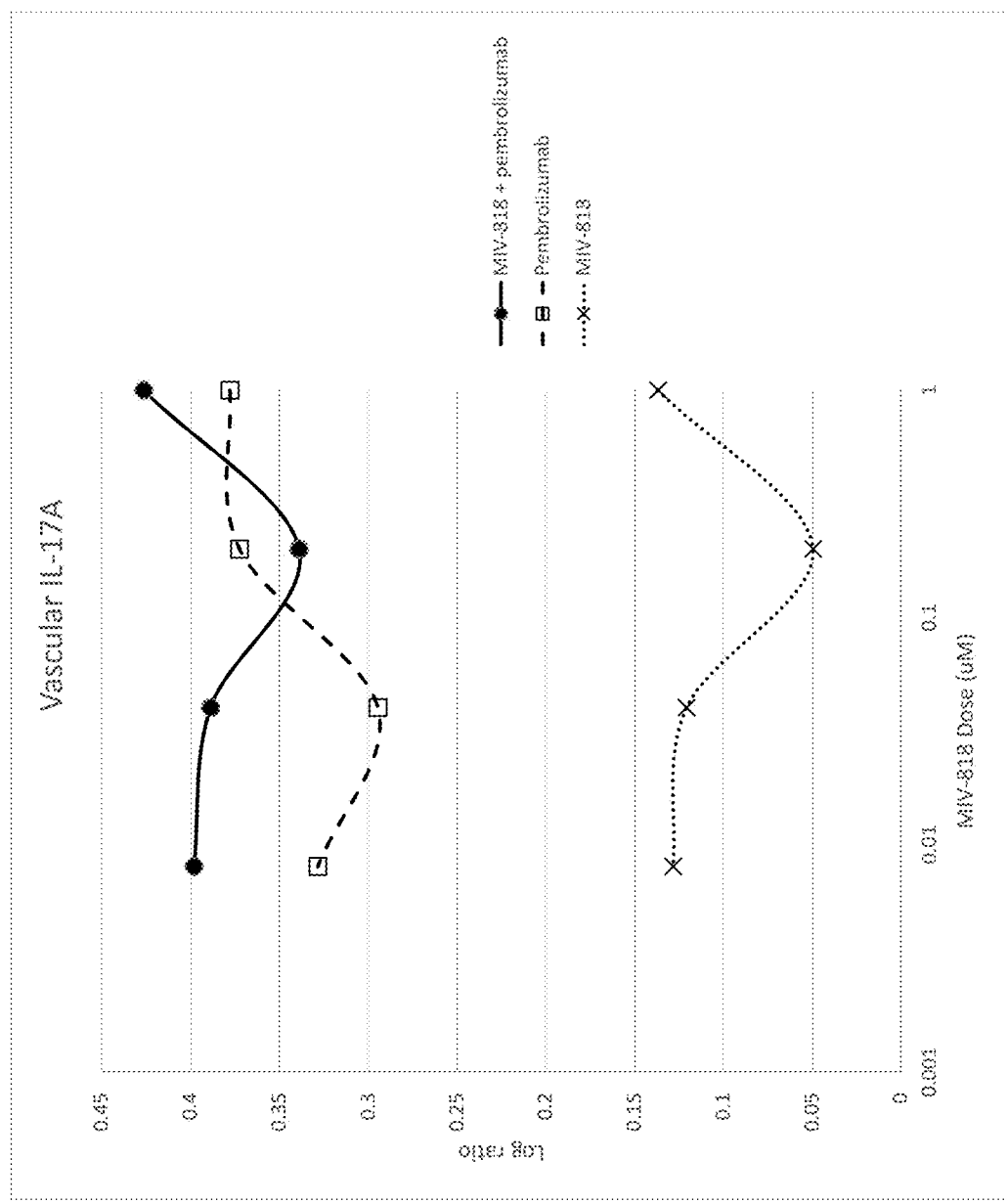
FIG. 11 is a plot corresponding to FIG. 10, but showing that vascular IL-17A is substantially unaffected by the combination.

The combination of MIV-818 and pembrolizumab shows a clear dose response enhanced IL-17A in the stromal HT-29 system, compared to either agent alone, indicative of induction of an enhanced anti-tumour immune response. In contrast, FIG. 11 shows that vascular IL-17A is substantially unaffected by the combination, consistent with the hypothesis that the Stro HT29 panel is of particular relevance to HCC, but importantly no evidence of antagonism is seen.

Figure 12:
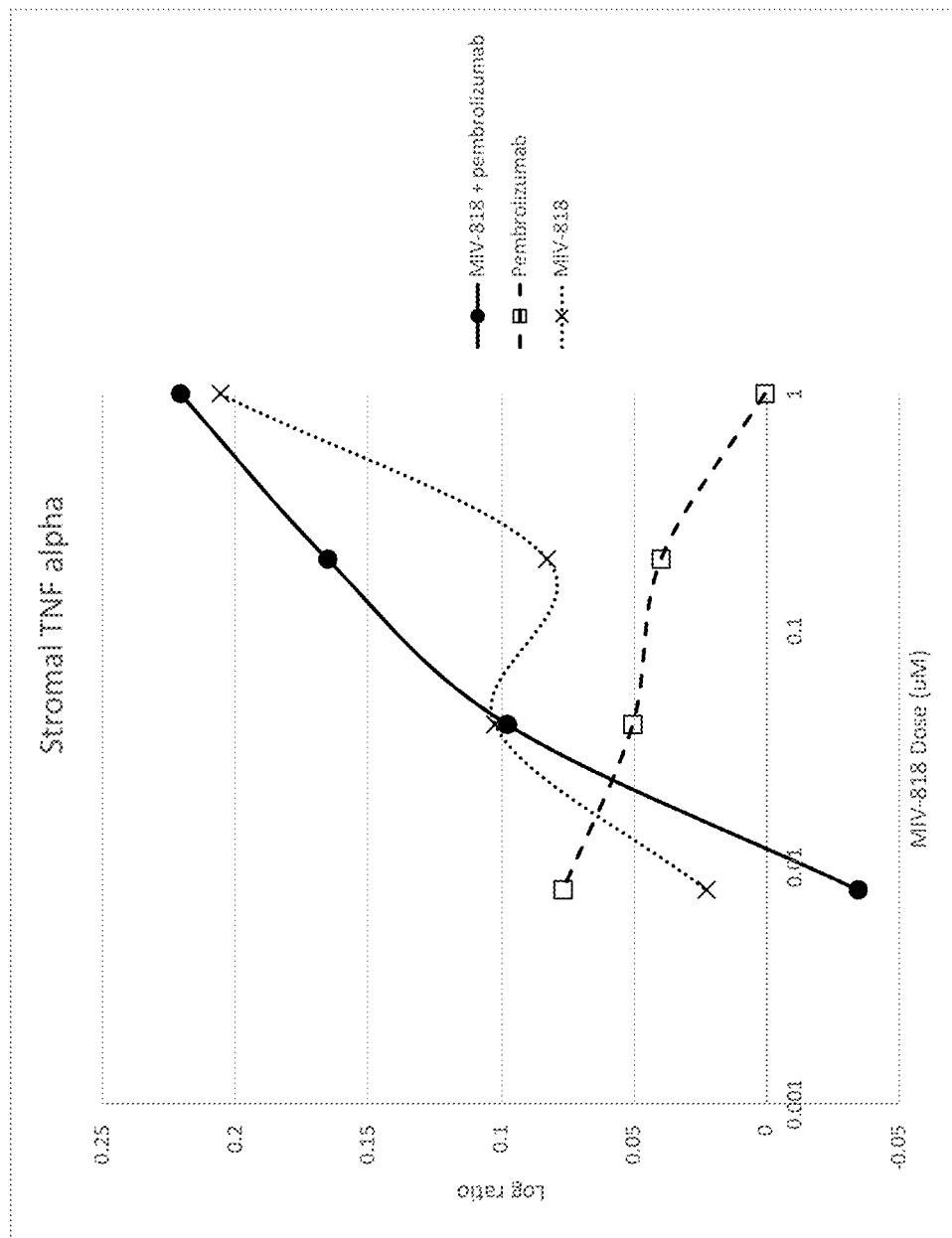
FIG. 12 is a plot showing the relationship between dose and effects of the components MIV-818 and pembrolizumab on stromal TNF alpha in the cell culture model of the tumour microenvironment.

FIG. 12 is a plot showing the relationship between dose and ratio of the components MIV-818 and pembrolizumab on stromal TNF alpha in the cell culture model of the tumour microenvironment. Tumour necrosis factor alpha (sTNFα) is a proinflammatory cytokine produced by macrophages, monocytes, neutrophils, T-cells, and NK cells that plays a major role in diseases involving systemic inflammation. In cancer, TNFα has pleotropic effects that are context dependent and include promotion of growth, survival, proliferation, angiogenesis and tumour cell death. Soluble TNFα (sTNFα) is categorized as an inflammation-related activity in the StroHT29 system modeling the interaction between the immune-stromal (fibroblasts) environment in the context of a colon cancer cell line (CRC HT29).

Figure 13:
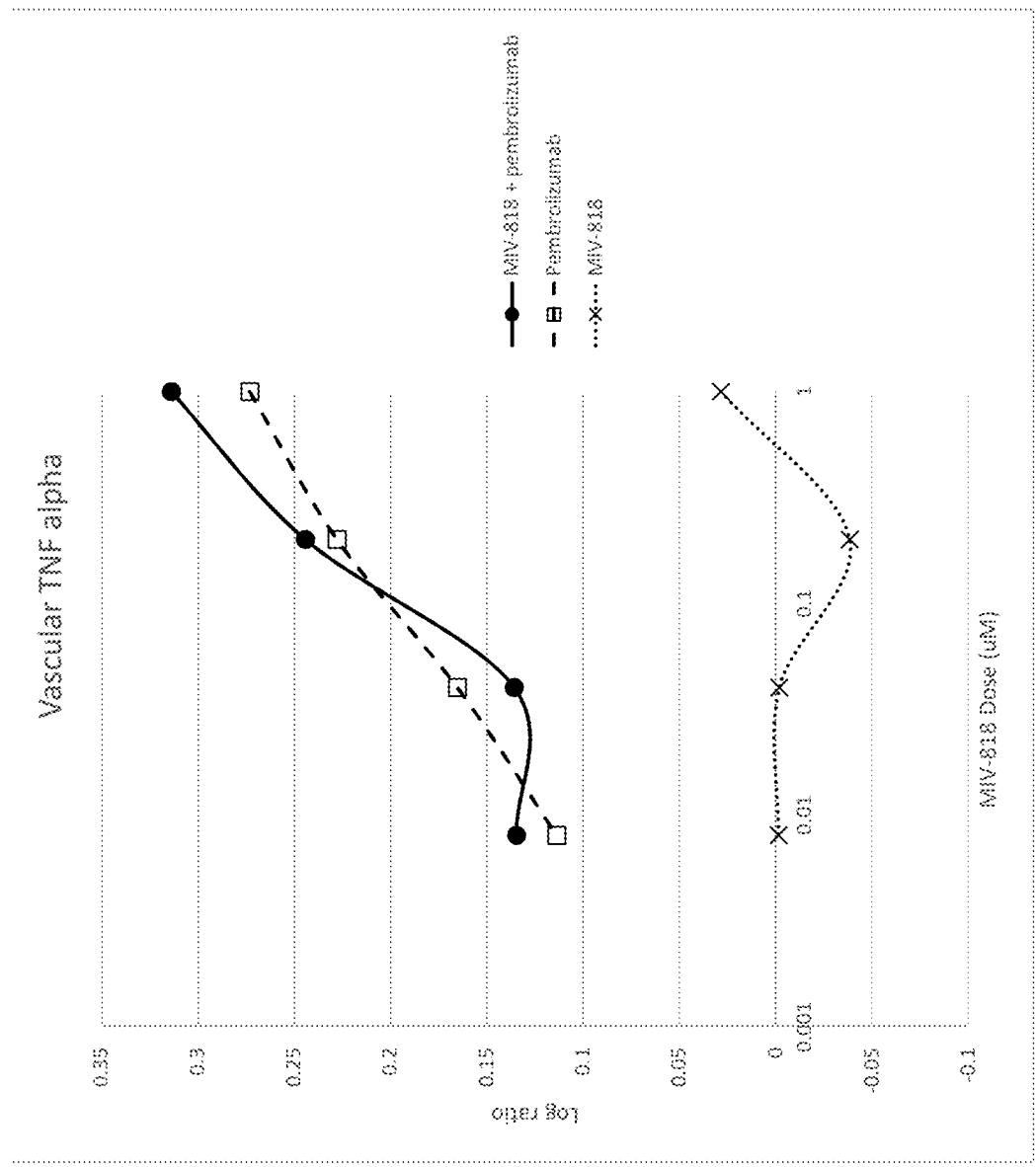
FIG. 13 is a plot corresponding to FIG. 12, but showing that vascular TNF alpha is substantially unaffected by the combination.

The combination of MIV-818 and pembrolizumab shows a clear dose response enhanced TNFα in the stromal HT-29 system, compared to pembrolizumab alone, indicative of induction of an enhanced anti-tumour immune response. In contrast, FIG. 13 implies that vascular TNF alpha is substantially unaffected by the combination, but importantly no evidence of antagonism is seen.

FIG. 14 is a plot showing the relationship between dose and ratio of the components MIV-818 and pembrolizumab on stromal IL-6 in the cell culture model of the tumour microenvironment. The addition of MIV-818 to pembrolizumab results in a decrease of the tumour-promoting cytokine IL-6 in contrast to the increase observed with pembrolizumab alone. Interleukin 6 (IL-6) is a secreted proinflammatory cytokine and acute phase reactant that is produced by fibroblasts, endothelial cells, T cells, B cells, and monocytes. In colorectal cancer, IL-6 promotes proliferation and suppresses apoptosis of tumour cells. Soluble IL-6 (siL-6) is categorized as an immune-related activity in the StroHT29 system modeling the interaction between the immune-stromal (fibroblasts) environment in the context of a colon cancer cell line (CRC HT29).

MIV-818 inhibits siL-6 in the stromal HT-29 system alone and in combination with pembrolizumb, in contrast to pembrolizumab alone, which leads to a modest enhancement of siL-6. FIG. 15 implies that vascular IL6 is substantially unaffected by the combination in this system.

Example 2

In Vitro Stimulation of IL-2 Expression in Immune-Stimulated Peripheral Blood Mononuclear Cell (PBMC) Cultures A key cytokine for T-cell proliferation and tumour cell killing during an immune-response is IL-2. The impact of various agents on the production of immune-cytokines can be tested in cultures of immune cells (PBMC) which are stimulated by super-antigens, e.g. with Staphylococcal Enterotoxin B (SEB), We observed, surprisingly considering the know mechanism of action, that MIV-818 induced IL-2 expression in such SEB-stimulated cultures in a dose-dependent manner, and that addition of anti-PD1 check-point inhibitor pembrolizumab enhanced the IL-2 expression. This suggests that a combination of MIV-818 with anti-PD(L)1 therapy would have an increased therapeutic efficacy when treating cancer.

Method

Human PBMC were isolated from three healthy donors, counted and plated at a uniform density. Cells were incubated with MIV-818, alone or in combination with Pembrolizumab, at up to six concentrations for 1 hour prior to stimulation. Appropriate controls were included: unstimulated cells, cells stimulated in the presence of media only (positive control), cells stimulated in the presence of a vehicle and cells stimulated in the presence of a reference compound at a single concentration. Cells were then incubated for five days with Staphylococcus Enterotoxin B (SEB) at a single concentration. Cell proliferation was quantified by tritiated thymidine incorporation. Culture supernatants were harvested after five days and stored until analysis of cytokine IL-2 by Luminex® assay. Each culture condition was established in triplicate. Multiplex readings were performed in singlicate on each culture well.

FIG. 16 is graph showing the increase in the cytokine IL-.2, critical for mounting a T-cell anti-tumour response, in a staphylococcus entero-toxin B stimulated PBMC culture. IL-2 expression is induced by MIV-818 alone and the enhanced IL-2 expression is observed with the addition of pembrolizumab.

Example 3

PBMC-Mediated Tumour Cell Killing

As a model for tumour cell killing by the immune-system, an in vitro model using isolated peripheral blood mononuclear cells (mainly T-cells) in which the T-cells are activated by stimulating the T-cell receptor (TCR) by anti-CD3 antibody. The T-cells will then perform cell-killing and the effect of adding compounds to this co-culture can be measured. MIV-818 was observed to enhance PBMC-mediated killing of the cancer cells, suggesting that MIV-818 induces an effect that synergizes with check-point inhibitor activity (pembrolizumab).

Method

Whole blood from three healthy donors was used. PBMC were isolated over a density gradient and counted before adding to NucLight Red labelled tumour targets at a defined E:T ratio in the presence of anti-CD3 stimulation. Tumour cell—PBMC co-cultures were incubated with test compounds at eight concentrations. Appropriate controls were included: PBMC alone, tumour cells alone, tumour cells/PBMC in the presence of a reference compound at a single concentration. All test conditions were also plated onto tumour cells in the absence of stimulated PBMC in order to detect direct compound-associated tumour cytotoxicity. Tumour killing was evaluated by counting viable NucLight positive tumour cells over time. In addition, a Caspase 3/7 dye was used to identify apoptotic tumour cells. Cultures were analysed using an IncuCyte ZOOM machine which allows real-time quantitative live cell fluorescent imaging. Co-cultures were imaged over 68 hrs. Each culture condition was established in triplicate. Cell culture supernatants were stored for optional cytokine analysis.

FIG. 17 is a graph showing the PBMC-mediated tumour cell killing activity in the presence of MIV-818 and pembrolizumab (apoptotic SK-OV-3 counts).

PBMC were isolated from 3 healthy donors and added to co-cultures with anti-CD3 stimulation and NucLight Red labelled SK-OV-3 tumour cells. Cultures were incubated in triplicate with 5000 nM MIV-818 or the combination of MIV-818+pembrolizumab alongside a vehicle control. SK-OV-3 apoptotic cell death was monitored in the co-culture system by imaging for 68 hours using the IncuCyte Zoom software. Data is displayed as mean values+/−SEM (three donors).

The embodiments described above are intended to be merely exemplary and those skilled in the art will recognize or will be able to ascertain using no more than routine experimentation, numerous equivalents of specific compounds, materials and procedures. All such equivalents are considered to be within the scope and are encompassed by the appended claims.

The invention claimed is:

1. A method of treatment of a liver cancer in a mammal in need thereof, comprising the administration of a therapeutically effective amount of a compound of the formula I:

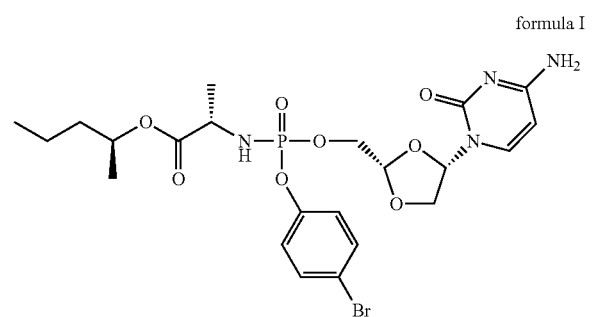 [SMILES: CCC[C@H](C)OC(=O)[C@H](C)NP(=O)(OC[C@H]1OC[C@@H](n2ccc(N)nc2=O)O1)Oc1ccc(Br)cc1]

formula I or a pharmaceutically acceptable salt thereof, with the concurrent or sequential treatment of the mammal with a therapeutically effective amount of a monoclonal antibody which blocks the binding of PD-L1 and/or PD-L2 to PD-1.

2. The method according to claim 1, wherein the monoclonal antibody is an anti-PD1 monoclonal antibody which is a humanized monoclonal IgG4 antibody.

3. The method according to claim 2, wherein the humanized monoclonal IgG4 antibody is pembrolizumab, pidilizumab, nivolumab, camrelizumab or tislelizumab.

4. The method according to claim 3, wherein the humanized monoclonal IgG4 antibody is pembrolizumab.

5. The method according to claim 3, wherein the humanized monoclonal IgG4 antibody is nivolumab.

6. The method according to claim 1, wherein the monoclonal antibody is an anti-PDL1 monoclonal antibody which is a humanized monoclonal IgG1 antibody.

7. The method according to claim 6, wherein the IgG1 antibody is atezolizumab, avelumab or durvalumab.

8. The method according to claim 7, wherein the IgG1 antibody is durvalumab.

9. The method according to claim 1, wherein the cancer is HCC.

10. The method according to claim 1, wherein the compound of formula I is administered orally and the monoclonal antibody is administered parenterally.

11. The method according to claim 1, wherein the compound is at least 90% ee of the diastereomer:

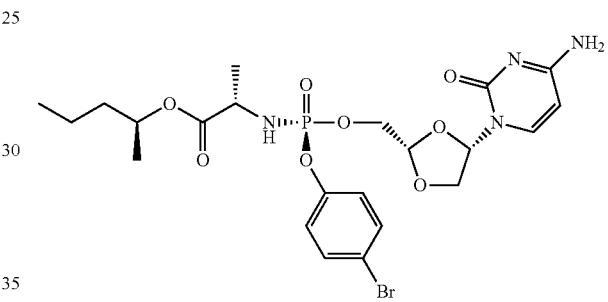

or a pharmaceutically acceptable salt thereof.

12. A method for treating a mammal afflicted with a primary or secondary liver tumour comprising cyclically administering to the mammal a therapeutically effective amount of a compound according to formula I or a pharmaceutically acceptable salt thereof and a therapeutically effective amount of a monoclonal antibody which blocks the binding of PD-L1 or PD-L2 to PD1, wherein the compound has the formula I:

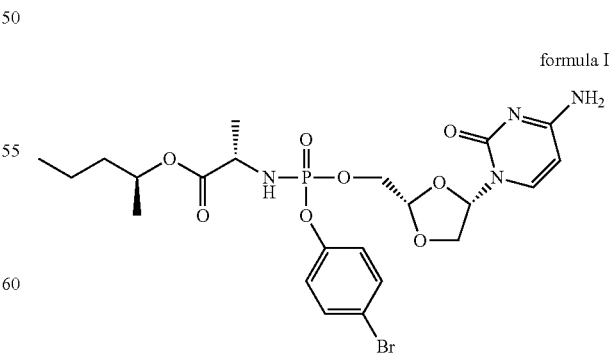

formula I and wherein the compound or a pharmaceutically acceptable salt thereof is administered orally and the antibody is administered parenterally.

13. A method of treating liver cancer in a human in need thereof, comprising administrating
(a) a therapeutically effective amount of a compound of the formula I:

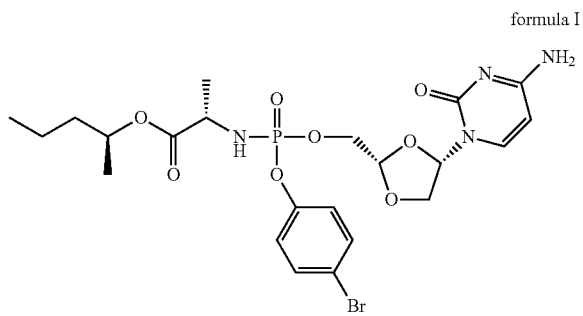 [SMILES: CCC[C@H](C)OC(=O)[C@H](C)NP(=O)(OC[C@H]1OC[C@@H](n2ccc(N)nc2=O)O1)Oc1ccc(Br)cc1]

formula I or a pharmaceutically acceptable salt thereof; and
(b) a therapeutically effective amount of an anti-PD-1, anti-PD-L1, and/or anti-PD-L2 monoclonal antibody comprising means for binding human PD-1.

14. The method according to claim 13, wherein the monoclonal antibody is a humanized monoclonal IgG4 antibody.

15. The method according to claim 13, wherein the monoclonal antibody is a humanized monoclonal IgG1 antibody.

16. The method according to claim 13, wherein the liver cancer is HCC.

17. The method according to claim 1, wherein the compound of formula I is administered orally and the monoclonal antibody is administered parenterally.

18. A method for treating liver cancer in a human afflicted with a primary or secondary liver tumour comprising cyclically administering to the human
(a) a therapeutically effective amount of a compound according to formula I

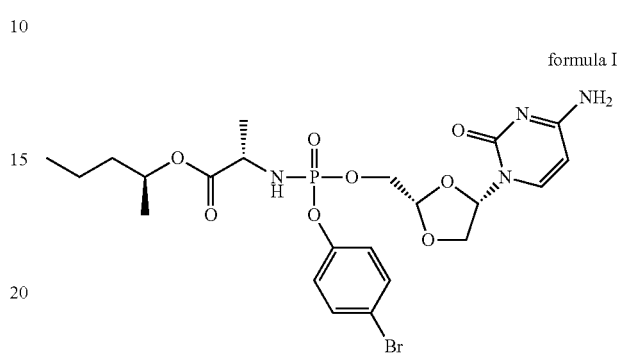

formula I or a pharmaceutically acceptable salt thereof; and
(b) a therapeutically effective amount of an anti-PD-1, anti-PD-L1, and/or anti-PD-L2 monoclonal antibody comprising means for binding human PD-1,
wherein the compound of (a) is administered orally and the antibody of (b) is administered parenterally.

* * * * *